(12) United States Patent
Guillemette

(10) Patent No.: US 11,540,760 B1
(45) Date of Patent: Jan. 3, 2023

(54) RETROFITTABLE AND PORTABLE COMMODE AND SYSTEMS FOR DETECTING, TRACKING, AND ALERTING HEALTH CHANGES

(71) Applicant: ENCEINTE HEALTH, INC., Ames, IA (US)

(72) Inventor: Andrew Connor Guillemette, Roland, IA (US)

(73) Assignee: ENCEINTE HEALTH, INC., Ames, IA (US)

( * ) Notice: Subject to any disclaimer, the term of this patent is extended or adjusted under 35 U.S.C. 154(b) by 203 days.

(21) Appl. No.: 16/866,353

(22) Filed: May 4, 2020

Related U.S. Application Data

(60) Provisional application No. 62/842,535, filed on May 3, 2019.

(51) Int. Cl.
| | |
|---|---|
| *A61B 5/00* | (2006.01) |
| *A61B 5/20* | (2006.01) |
| *A47K 13/10* | (2006.01) |
| *A47K 13/24* | (2006.01) |
| *A47K 13/12* | (2006.01) |
| *G16H 50/30* | (2018.01) |

(52) U.S. Cl.
CPC ............. *A61B 5/20* (2013.01); *A47K 13/105* (2013.01); *A47K 13/12* (2013.01); *A47K 13/24* (2013.01); *A61B 5/002* (2013.01); *A61B 5/0022* (2013.01); *A61B 5/749* (2013.01); *G16H 50/30* (2018.01); *A61B 2562/0252* (2013.01)

(58) Field of Classification Search
CPC ......... A61B 5/20; A61B 5/002; A61B 5/0022; A61B 5/749; A61B 2562/0252; A47K 13/105; A47K 13/12; A47K 13/24; G16H 50/30
See application file for complete search history.

(56) References Cited

U.S. PATENT DOCUMENTS

| | | | |
|---|---|---|---|
| 5,410,471 | A | 4/1995 | Alyfuku et al. |
| 6,984,207 | B1 | 1/2006 | Sullivan et al. |
| 8,827,918 | B2 | 9/2014 | Kim et al. |
| 8,983,854 | B2 | 3/2015 | Park et al. |
| 9,756,297 | B1 * | 9/2017 | Clements ........... H04N 5/23296 |
| 10,064,582 | B2 | 9/2018 | Rogers |
| 10,130,293 | B2 | 11/2018 | Hidas |
| 10,178,973 | B2 | 1/2019 | Venkatraman et al. |

(Continued)

FOREIGN PATENT DOCUMENTS

| | | |
|---|---|---|
| CN | 203749319 U | 8/2014 |
| CN | 203834617 U | 9/2014 |

(Continued)

*Primary Examiner* — Hongmin Fan
(74) *Attorney, Agent, or Firm* — Nyemaster Goode, P.C.

(57) ABSTRACT

A retrofittable commode attachment device that automatically measures and charts electronically one or more types of health data. The device includes a base platform with a back portion, a left side portion, a right side portion and a front portion, a plurality of load cells on the left side of the base platform and a plurality of load cells on the right side of the base platform, at least one microphone, at least one camera, and at least two commode connector brackets that engage the horizontal support of a commode and the base platform is positioned below the toilet seat of the commode and is not part of the toilet seat.

20 Claims, 20 Drawing Sheets

(56) References Cited

U.S. PATENT DOCUMENTS

| | | |
|---|---|---|
| 10,216,905 B2 | 2/2019 | Rogers |
| 10,292,658 B2 | 5/2019 | Borkholder et al. |
| 10,376,246 B2 | 8/2019 | Kashyap et al. |
| 10,383,576 B2 | 8/2019 | Hall et al. |
| 10,542,937 B2 | 1/2020 | Hall et al. |
| 2006/0258915 A1 | 11/2006 | Ueda et al. |
| 2016/0374619 A1* | 12/2016 | Borkholder ............ A61B 5/318 600/301 |
| 2018/0092602 A1 | 4/2018 | Hall et al. |
| 2019/0008457 A1 | 1/2019 | Hall et al. |
| 2019/0231271 A1 | 8/2019 | Borkholder et al. |

FOREIGN PATENT DOCUMENTS

| | | | |
|---|---|---|---|
| CN | 104131607 A | 11/2014 | |
| CN | 204318745 U | 5/2015 | |
| CN | 105286712 A | 2/2016 | |
| CN | 105507394 A | 4/2016 | |
| CN | 105653838 A | 6/2016 | |
| CN | 106930380 * | 7/2017 | ............... E03D 9/00 |
| CN | 206324731 U | 7/2017 | |
| CN | 206328830 U | 7/2017 | |
| CN | 107224239 A | 10/2017 | |
| CN | 107796473 * | 3/2018 | ............... G01N 9/02 |
| CN | 108498087 A | 9/2018 | |
| CN | 108661139 A | 10/2018 | |
| CN | 108703708 A | 10/2018 | |
| CN | 109653323 A * | 4/2019 | ............ G01N 33/48 |
| KR | 20200071957 * | 6/2020 | ........... A61B 5/0059 |
| WO | 2018187790 A2 | 10/2018 | |
| WO | 2019051672 A1 | 3/2019 | |

* cited by examiner

SMART TOILET 204

&& DASHBOARD
&+ NEW RESIDENT
⏱ SNF SUMMARY
⊕ NEW ADMISSION RESIDENTS

← BACK

| MATT |
| M ROOM: 314 |

— 230

| < | FEB 8, 2020 | > |

— 228

≡ HISTORICAL SUMMARY   ⚙ INTERVENTION   & PROFILE

— 224

TOTAL VISITS: 3
AVERAGE BODY WEIGHT: 121 lbs
AVERAGE URINE VOLUME: 30 mL
URINE VOLUME/VISIT: 30 mL

— 222                         — 234

| VISIT | TIME START | URINE VOLUME | STOOL CLASSIFICATION | BODY WEIGHT | ACTIONS |
|---|---|---|---|---|---|
| 0 | X HOURS AGO | 11 mL | 4 | 252 lbs | DETAILS |
| 1 | X HOURS AGO | 7 mL | 4 | 252 lbs | DETAILS |
| 2 | X HOURS AGO | 19 mL | 4 | 247 lbs | DETAILS |
| 3 | X HOURS AGO | 11 mL | 4 | 247 lbs | DETAILS |
| 4 | X HOURS AGO | 3 mL | 4 | 208 lbs | DETAILS |
| 5 | X HOURS AGO | 0 mL | 4 | N/A lbs | DETAILS |
| 6 | X HOURS AGO | 15 mL | 4 | 247 lbs | DETAILS |
| 7 | X HOURS AGO | 11 mL | 4 | 239 lbs | DETAILS |
| 8 | X HOURS AGO | 16 mL | 4 | 253 lbs | DETAILS |
| 9 | X HOURS AGO | 14 mL | 4 | 232 lbs | DETAILS |
| 10 | X HOURS AGO | 15 mL | 4 | 247 lbs | DETAILS |

ALERTS FOR MATT — 210

RETROFITTABLE AND PORTABLE COMMODE AND SYSTEMS FOR DETECTING, TRACKING, AND ALERTING HEALTH CHANGES

CROSS-REFERENCE TO RELATED APPLICATION

This application claims benefit from and priority to U.S. Ser. No. 62/842,535, filed on May 3, 2019, entitled "Smart Toilet Seat that can detect health problems through the change in sensor data," the disclosure of which is hereby incorporated herein by reference in its entirety.

BACKGROUND

In a Nursing Home/Skilled Nursing Facility/Health Care Center, residents have three ways in which they can go to the bathroom. A resident who still has quite a bit of mobility will go to the restroom on a normal/standard toilet. A resident who has a problem with mobility (mainly bending at the waist) will have to sit on an elevated toilet seat. This can be done in a few ways. The first way you can do this is by getting a toilet seat riser that drops over the existing toilet seat. The second way is to straddle a commode over the toilet and adjust it to the right height recommended by the doctor. The third way to use the restroom is via a commode by the resident's bed. If the resident is unable to travel very far it is a lot easier to transition the resident from the bed onto a commode which is at the same height as the bed.

A standard commode 10 without any device/system of the present disclosure is generally shown in FIG. 1. An ordinary commode typically has upright support legs 12, a horizontal support cross bar or bars 14, a bucket support frame 16 that holds and suspends a urine and bowel movement collection bucket 20. A chute 18 may be employed too. Existing commodes typically have a toilet seat 22 and toilet lid 24. They further typically contain handles 26 and often rubber slip resistant feet 28.

When a resident goes to the bathroom next to the bed, the stool and urine will be collected in a bucket. Once the resident is finished a CNA (Certified Nursing Assistant) will come collect the bucket and empty it in the toilet.

The current typical way medical professionals chart the bowel and bladder process is through manual observation by the CNA. When a CNA is charting for bowel movements they are normally answering pre-selected yes or no questions. When a new resident of a care facility is added to the care facility a bowel and bladder nurse determines what he/she wants to keep tabs on regarding the new resident. As a result, more often than not, if the right question or questions are not asked signs of health problems often go missed. There is really no current way a CNA today could chart and keep track of the numerous variables measured by the systems and devices of the present disclosure in each visit for every resident. Even in the unlikely event the data is attempted to be captured, normally CNAs or direct care staff members will chart this data when it's more convenient instead of when it would be more accurate to do so—right after a visit. This manual charting process has worked for a while but it's not a scalable solution. Additionally, there are at least two things wrong with this process. First, CNAs are not trained to a national standard and are not very well educated when it comes to understanding what goes on inside the toilet bowl. Second, CNAs do not have enough time to be present at each bathroom event. This lack of time means events go missed and most events are logged over 30 minutes after being observed and/or too quickly/not carefully, which causes inaccuracies.

The individuals who really understand what is going on inside the toilet bowl are the bowel and bladder nurse, the clinicians, the director of nursing, not the typical CNA. The industry understands the bowel and urinary data is important. They train certain people to understand what the data and information means, but they are often relying on individuals who are not trained and/or overworked to attempt to accurately obtain this data and log it in a timely manner. In reality the current process results in getting subjective and/or incomplete data instead of solid data and real analytics. As a result, data is often not used or might be ignored by health professionals who might dismiss it as unreliable. This may even lead to residents of care facilities in particular, but users in general, to have unnecessary emergency room visits and/or be given unnecessary medication or other unnecessary and/or missed medical attention occurs.

SUMMARY

One aspect of the present disclosure includes a retrofittable commode attachment device for automatically measuring and charting electronically one or more types of health data that includes a base platform comprising a back portion, a left side portion, a right side portion and a front portion, a plurality of load cells on the left side of the base platform and a plurality of load cells on the right side of the base platform, at least one microphone, at least one camera, and at least two commode connector brackets that engage the horizontal support of a commode. The base platform is positioned below the toilet seat of the commode and is not part of the toilet seat. The load cells are in signal communication with a signal transmitter engaged with the base platform that delivers data via a wired data signal transfer system or a wireless data signal transfer system to a server system located remote from the retrofittable commode attachment device that stores the health data transferred to it from the retrofittable commode attachment device. The at least one microphone and at least one camera are within a housing mounted to the back portion of the base platform and extending away from the back portion such that the camera and microphone are positioned to view an inside of a toilet bowl.

Another aspect of the present disclosure includes a commode attachment system for automatically (without direct human involvement) measuring and charting electronically one or more types of health data comprising: a remote data server having analytics software that analyze data received from a commode attachment data collection device and accessible by a health care professional using a healthcare professional user interface. The graphical user interface that is displayed to a healthcare professional displays data related to health data collected by the commode attachment device and conveyed from the commode attachment device to the remote data server. The commode attachment data collection device is not typically a portion of the toilet seat or lid. The commode attachment data collection device typically includes a base platform comprising a back portion, a left side portion, a right side portion and a front portion, a plurality of load cells on the left side of the base platform and a plurality of load cells on the right side of the base platform, at least one microphone, at least one camera, and at least two commode connector brackets that engage the horizontal support of a commode. The base platform is positioned below the toilet seat of the commode and is not typically part of the toilet seat. The load cells are in signal communication with a signal transmitter engaged with the base platform that delivers data via a wired data signal transfer system or a wireless data signal transfer system to a server system located remote from the retrofittable commode attachment device that stores the health data transferred to it from the retrofittable commode attachment device. The at least one microphone and at least one camera are typically spaced within a housing mounted to the back portion of the base platform and the housing extends away from the back portion such that the camera and microphone are positioned to view an inside of a toilet bowel.

Yet another aspect of the present invention includes a commode attachment system for automatically measuring and charting electronically one or more types of health data. The system typically includes a remote data server having analytics software that analyze data received from a commode attachment data collection device and accessible by a health care professional using a health care professional user interface, wherein the professional user interface displays data related to health data collected by the commode attachment device and conveyed from the commode attachment device to the remote data server. The commode attachment data collection device is not typically a portion of the toilet seat or lid. The commode attachment data collection device typically includes a base platform comprising a back portion, a left side portion, a right side portion and a front portion, a plurality of load cells on the left side of the base platform and a plurality of load cells on the right side of the base platform, at least one microphone, at least one camera, and at least two commode connector brackets that engage the horizontal support of a commode. The base platform is positioned below the toilet seat of the commode. The load cells are in signal communication with a signal transmitter engaged with the base platform that delivers data via a wired data signal transfer system or a wireless data signal transfer system to a server system located remote from the commode attachment device that stores the health data transferred to it from the commode attachment device. The at least one microphone and at least one camera are typically spaced within a housing that is mounted to the back portion of the base platform and extending away from the back portion such that the camera and microphone are positioned to view an inside of a toilet bowel. The system further may include a scale chosen from: (1) a set of foot scales that includes a first foot scale rotatably engaged with a first front leg of a commode and a second foot scale rotatably engaged with a second front leg of the commode or (2) a planar pad engaged with both the first front leg of the commode and the second front leg of the commode such that the planar pad is moveable between a vertical position where the pad is proximate a length of the first front leg and a length of a second front leg and a horizontal position against the floor or other surface that the first front leg and the second front leg is resting on. When employed, the planar pad typically includes a plurality of load cells and the first foot scale typically includes a load cell and the second foot scale typically includes a load cell. The commode attachment device records and transmits to at least the health care data of different types chosen from the group consisting of: weight of the user, weight of urine, timing of urine stream, weight of stool, nature of the stool, shifting of weight of the user on the device while seated on the device, mounting forces of each load cell as a user sits on the toilet seat, dismounting forces of each load cell as the user lifts off from the toilet seat, and the weight of the user and also associates a time when each piece of data is collected or measured where the time is when an individual user of the commode attachment device used the commode and an event causing the data occurred.

These and other aspects, objects, and features of the present invention will be understood and appreciated by those skilled in the art upon studying the following specification, claims, and appended drawings.

BRIEF DESCRIPTION OF THE DRAWINGS

In the drawings:

FIG. 19 is another exemplary daily summary for a specific user of the commode device of the present disclosure showing another day's data.

FIG. 20 shows a display detailed view of an individual urination and/or stool event that allows the user to actually view the urination and/or bowel movement event via highlight images of the event and/or provide the ability to watch and see the event as it occurred via video stream.

DETAILED DESCRIPTION

To fully automate the bowel and bladder charting process and eliminate the manual charting process done by CNAs within a health care facility, one must be able to log and chart all data across each platform and at each instance of a patient going to the bathroom regardless of location—either a toilet or a commode. To do this, a system needs an untethered system having the ability to collect the same health data that a smart seat can but outside the bathroom setting as well as in the bathroom setting. The retrofittable devices/systems of the present disclosure seat will also have the ability to not only collect data outside the bathroom in the care facility, but the present invention is mobile, enabling it to easily collect a residents data as the resident heads home for a holiday weekend or any other location.

Figure 2:
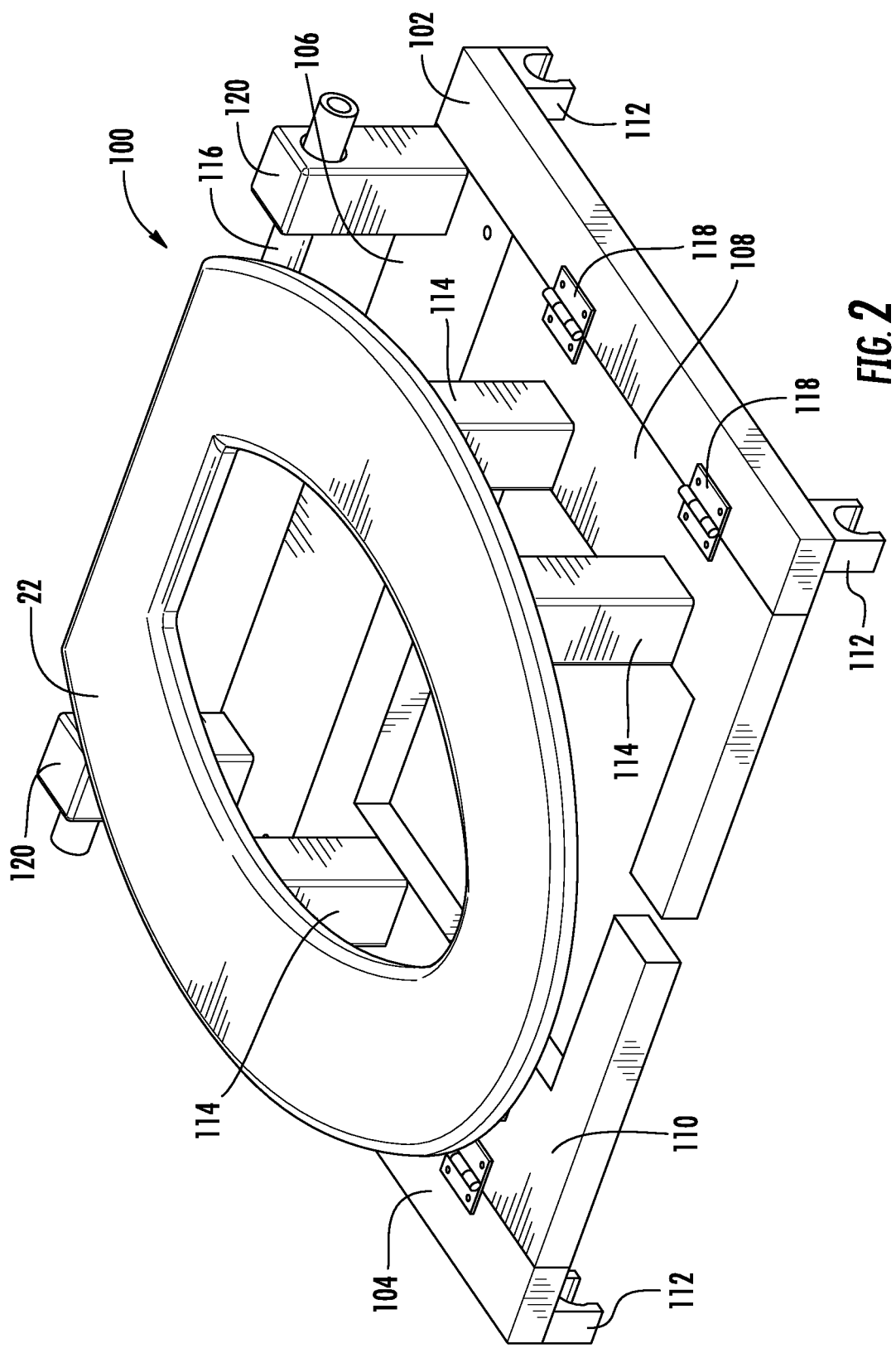
FIG. 2 is a perspective view of a retrofittable commode attachment device that is a raised device according to an aspect of the present disclosure.
Figure 3:
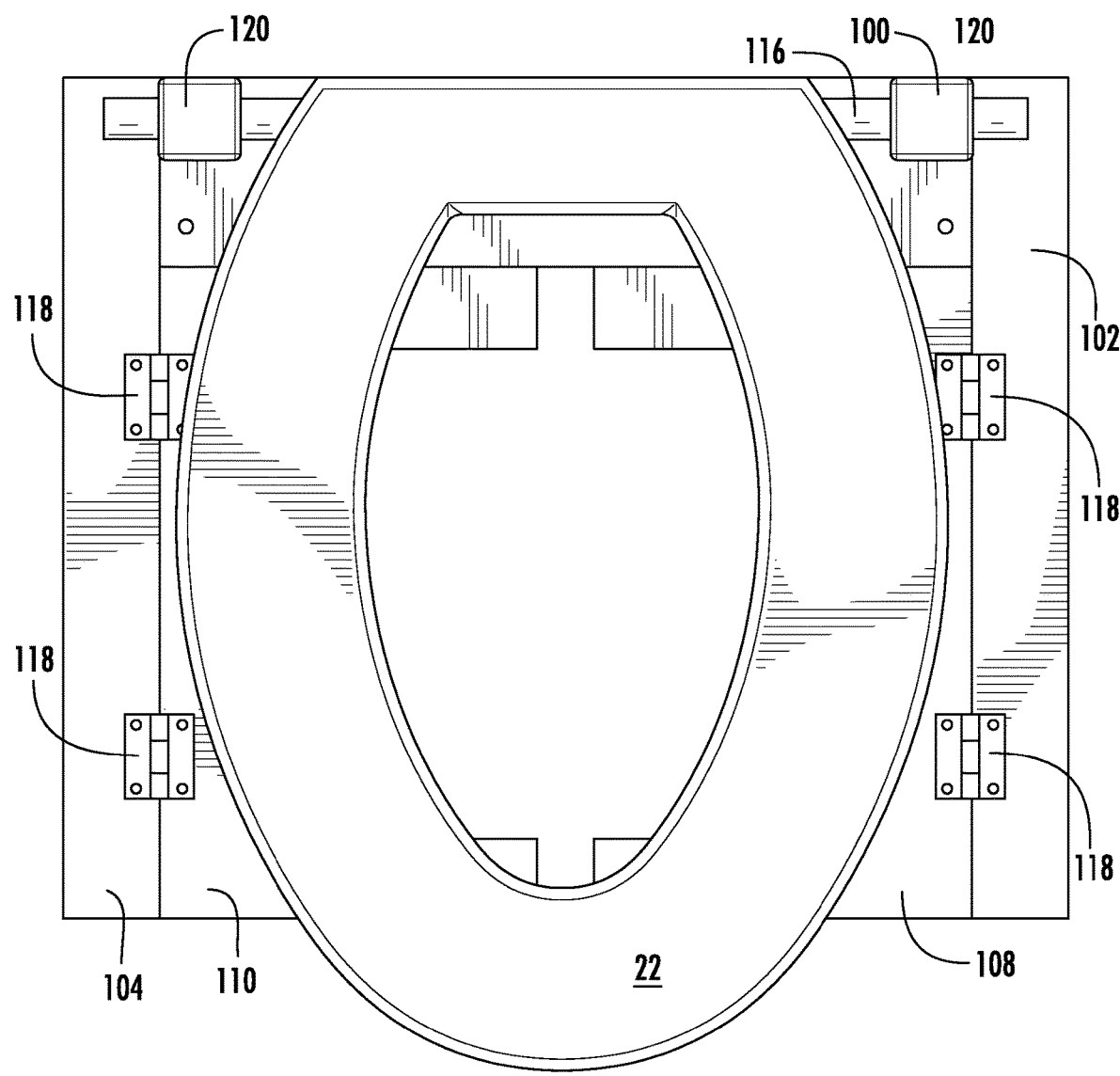
FIG. 3 is a top view of the retrofittable commode attachment device of FIG. 2.

For purposes of description herein, the terms "upper," "lower," "right," "left," "rear," "front," "vertical," "horizontal," and derivatives thereof shall relate to the invention as oriented in FIG. 2. However, it is to be understood that the disclosed devices/systems and the claimed invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 4:
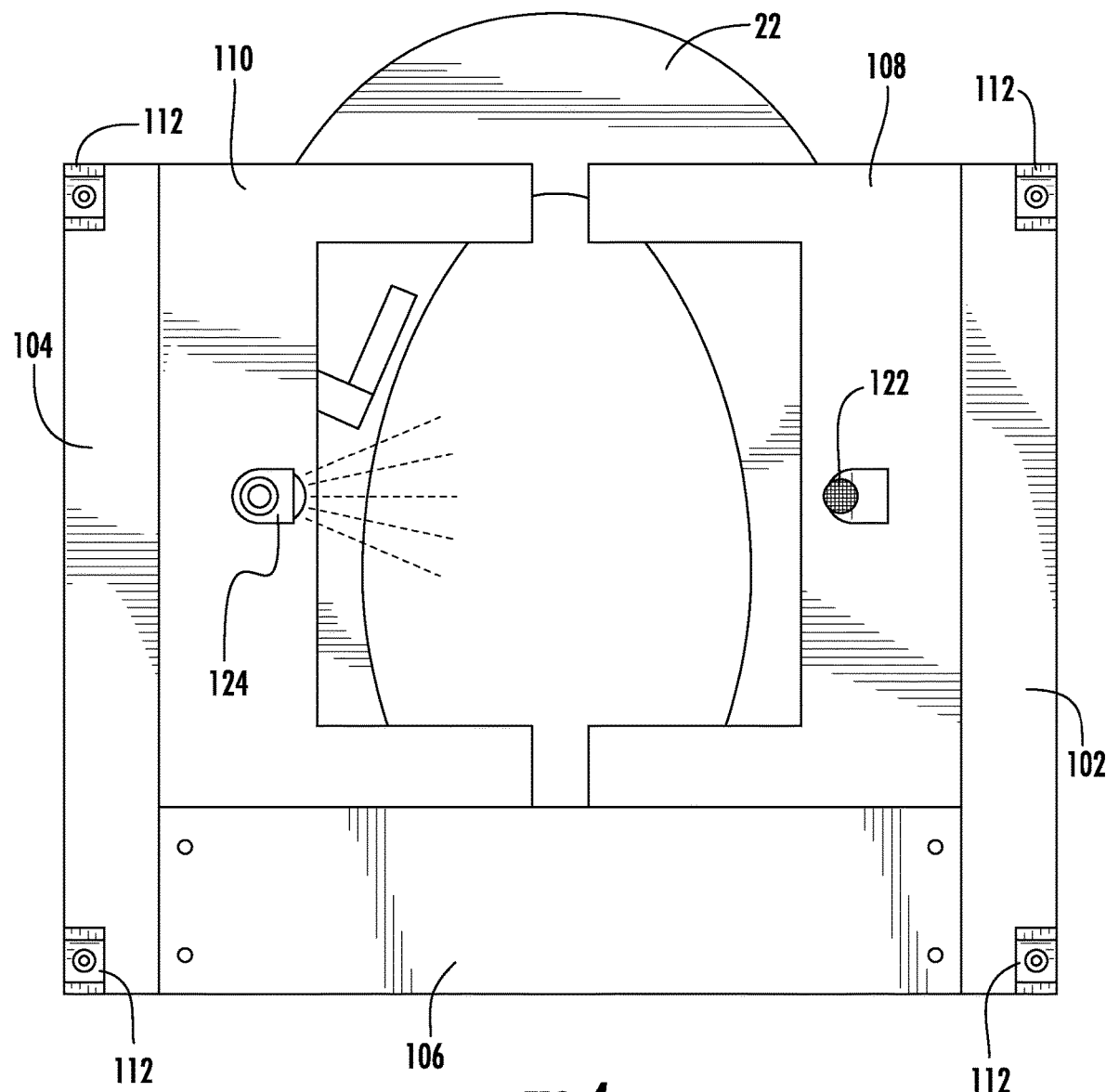
FIG. 4 is a bottom view of the retrofittable commode attachment device of FIG. 2.
Figure 5:
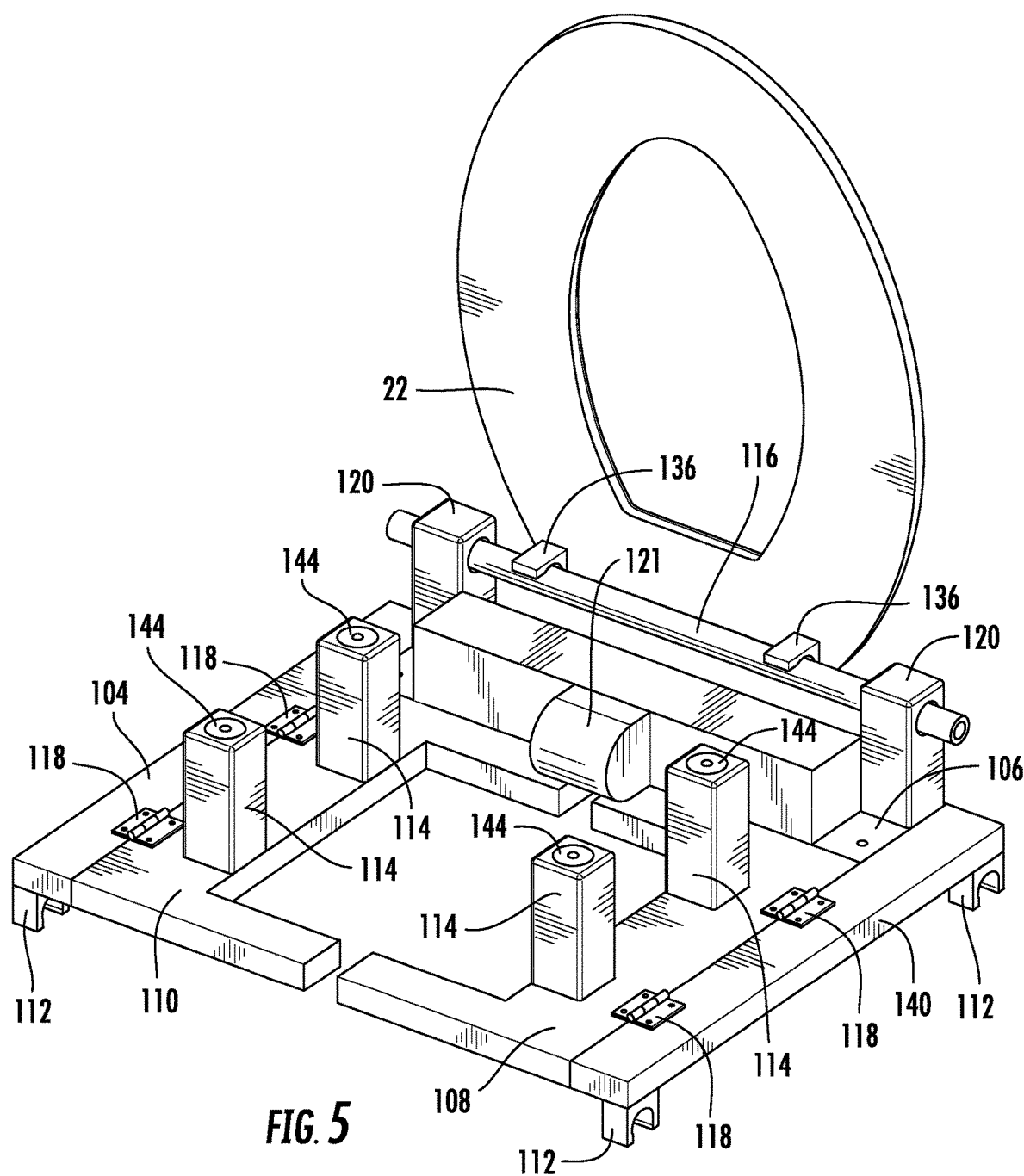
FIG. 5 is a perspective view of a retrofittable commode attachment device of the present disclosure showing a separate data collection sensor housing affixed to the back section of the frame of the device and with the toilet seat in the upright position.

As shown in FIGS. 2-15, the retrofittable commode devices/systems 100 of the present disclosure typically include the use of a sensor platform that uses load cells 144, at least one microphone 122, and at least one camera 124. The cameras can be RGB and thermal cameras, but can also include ECG (electrocardiography) sensors that measure the bio-potential generated by electrical signals that control the expansion and contraction of heart chambers and/or PPG (photoplethysmography) as well. The camera(s) and microphone(s) can be placed around the perimeter of the retrofittable commode devices of the present disclosure, typically on the underside of it, as shown in FIG. 4, but more typically within a housing 121 (see FIG. 5) of the removable commode devices of the present disclosure. The camera(s) can be hidden behind some clear glass that has a hydrophobic surface. The microphone(s) can be concealed by a hydrophobic mesh like what waterproof speakers use. The devices of the present disclosure often include a right side support 102, a left side support 104, a rear support 106, a right side retractable section 108, and a left side retractable section 110. The retractable sections may be affixed in a moveable fashion to the right and left side support sections. The commodes most often used in connection with the devices of the present disclosure typically include horizontal handle reinforcing supports 140 as well as horizontal supports bracing the left and right side retractable sections 141, and of the present disclosure. The retractable sections are typically hingedly connected to the side supports using one or more hinges 118 on each side of the device. The retractable sections can also be concealably slidable into and out of a compartment within the interior of the left and right side sections. In either case, the retractable sections are moveable between a retracted or cavity expanding position by hand and without the use of tools. This retracted or cavity expanding position is used to allow for ready access and easy removal of the bucket 20 when the bucket contains urine or stool without having to remove the device from engagement with the rear horizontal support cross bar each time. In the case of the embodiment of the present disclosure shown in FIG. 15, there is no support section or retractable sections. Instead, the system is spaced under the toilet seat and designed to matingly engage the recessed cavity 304 of the seat. This will be discussed in greater detail below.

The devices and systems of the present disclosure may also integrate with one or more wearable devices that could also provide data independently to the remote sever systems of the present disclosure. For example, a FITBIT®, health watch, blood pressure cuff, and/or glucose monitors can also be used to provide continuous vitals such as heart rate, ECG, respiration rate, Sp02 (peripheral capillary oxygen saturation) and step count. The systems of the present disclosure can also typically use the data tracked by the devices of the present disclosure and the one or more wearable health tracking or data recording devices to record, calculate and analyze derived vitals such as calories burned, heart rate variability, perfusion index, activity level, and sleep quality.

In the case of the device shown in FIGS. 2-12, the device employs a plurality of load cells 144. The load cells are typically spaced within seat supports 114 that extend upward from the right side retractable section 108 and the left side retractable section 110. Each retractable section typically contains two such supports each with a single load cell, which allows the load cells to be spaced about the toilet seat with two on each side, one proximate the front of the seat and one proximate the back of the seat on each side while in use. Conceivably, the seat supports 114 may be adjustable, but this is not typically the case since it is better to have the load cells properly calibrated and having the supports moveable in height might allow for variability in the measurements received from the load cells based on something other than the weight of the forces applied by the user of the device. More load cells may be employed on each side as well as a single load cell, but due to better data collection and cost two load cells and supports on each side are typically employed. The use of a greater number of load cells spaced about the perimeter of the toilet seat will allow for more precision of the data collected when a user mounts and dismounts the toilet seat. This data can be significant and therefore, in some instances, more load cells, including load cells spaced evenly around the entire perimeter of the toilet seat held by supports or perhaps an overall matching support structure that matches and mates with the toilet seat, may be employed instead of individual supports. The use of a greater number of load cells is more typically done in the case of the device shown in FIG. 15, which employs the load cells 144 into or on the surface of the device 300.

Figure 13:
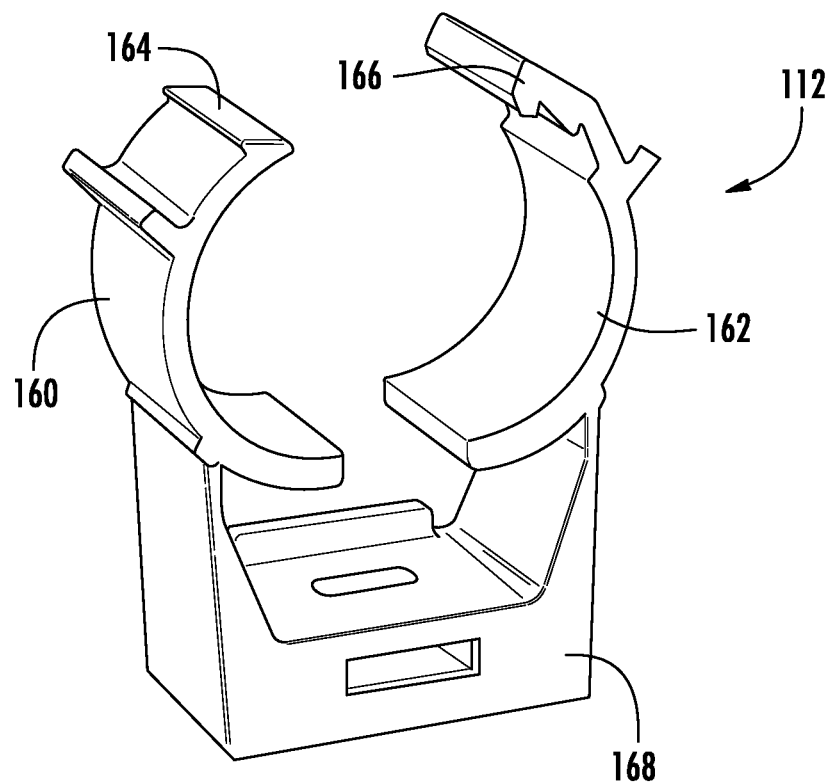
FIG. 13 is a perspective view of a snap engagement device for attachment of the retrofittable devices of the present disclosure to affix themselves to a horizontal support cross bar of a commode.

As shown in FIGS. 2-12, the devices use at least two upwardly extending bar supports that have cavities that receive a toilet seat and lid engaging bar 116. While the snap engagement devices 112 affixed to the bottom surface and typically proximate the corner sections or corners of the device engage the horizontal support cross bars after the existing toilet seat and lid are removed. The snap engagement devices 112, as shown in FIG. 13, have a first archuous section 160, a second archuous section 162, a base 168, a snap fit engagement lip section 164 and a snap fit grasping end 166 that receives the snap fit engagement lip section 164. The snap engagement devices are such that they are able to be releasably engaged with horizontal support bars of the commode regardless of the diameter of the support bars. The snap engagement devices may be engaged and disengaged from the support bars by hand and without the use of tools. The existing toilet seat and lid are re-affixed to the device's own toilet seat and lid engagement bar in the device shown in FIGS. 2-12.

When utilized, the overall sensor platform incorporating the left and right side supports, the rear support(s) and the retractable/moveable sections 108, 110. The overall sensor platform is typically affixed onto an existing commode frame using a plurality of snap engagement devices. The device shown in FIGS. 2-12 of present disclosure is not generally designed to come with a toilet seat or toilet seat lid. Instead, the devices of the present disclosure shown in these figures is purposefully designed to work with the existing commode seats and lids. This design keeps hardware costs down and make for an easy installation process and more widespread adoption of the use of the device since an overall commode with data sensors already built therein is not necessary. Conceivably, the system could be used and incorporated into an overall toilet seat with or without a lid, but this is not the primary embodiment of the present disclosure. If done, it is presently contemplated that the device of the present disclosure would be affixable in a rotatable manner onto the rear horizontal support frame and under an existing toilet seat of the commode or toilet—see FIG. 15, for example. In the case of the embodiment of FIG. 15, the under toilet seat retrofit device may be used in connection with a conventional toilet seat as well as a commode. This provides an even more comprehensive solution for tracking all urination and bowel movement and other health care data.

Figure 1:
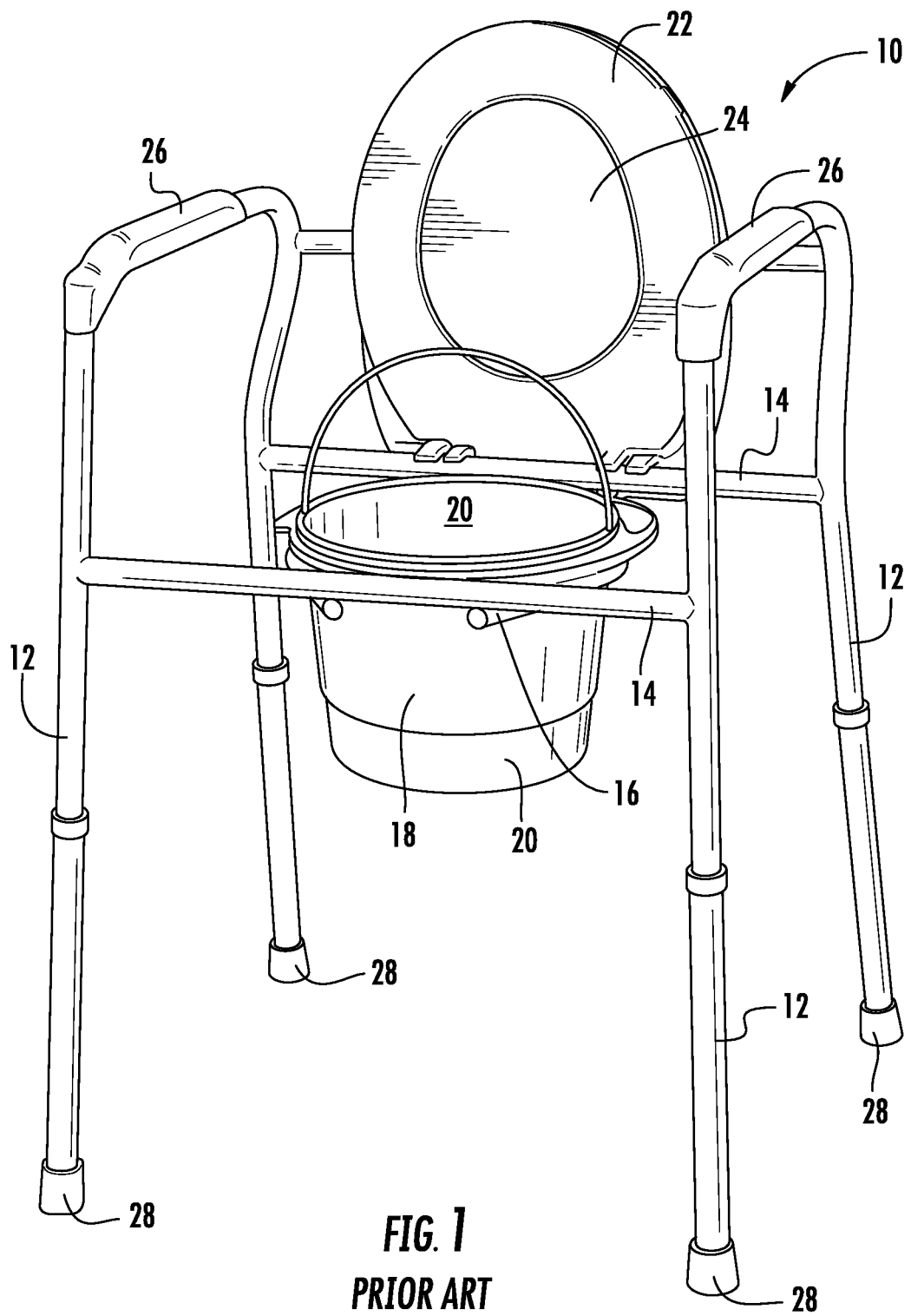
FIG. 1 is a perspective view of a prior art commode.

As you can see in the figure (right), all standard commode frames (see FIG. 1, for example) consist of the same size diameter pipe, and all toilet seats and toilet lids are designed to snap right onto the frame. To install the devices of the present disclosure, a user will first remove/pop off the existing seat and lid of the commode. Once that step is done, the user engages the device of the present disclosure into engagement with the commode. This is done by snapping one side of the device and then the other using the snap engagement devices 158 into engagement with the horizontal support cross bars 14. Once the frame is snapped in, the lid 24 and toilet seat 22 are snapped back into engagement with the commode's toilet seat and lid engagement bar 116 to complete the installation using the toilet seat engagement clips/brackets that allow for rotatable motion of the seat and lid.

Figure 6:
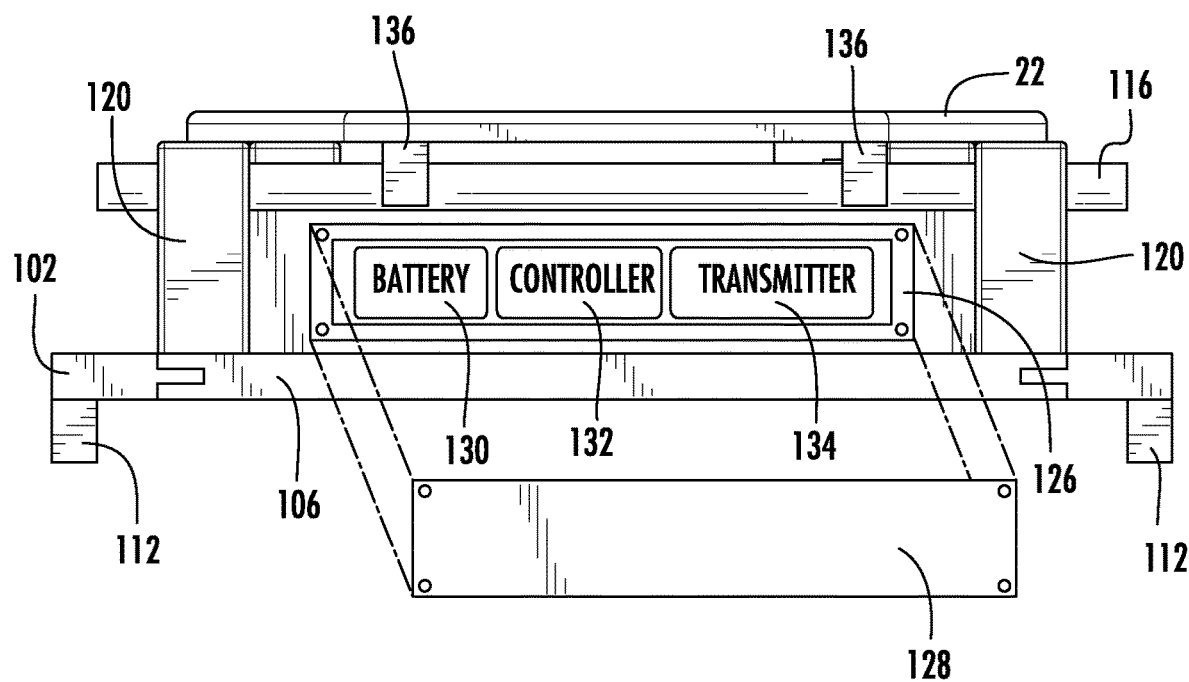
FIG. 6 is an elevated rear view of a retrofittable commode attachment device of the present disclosure showing a data/electrical component compartment with a water tight sealable cover.
Figure 7:
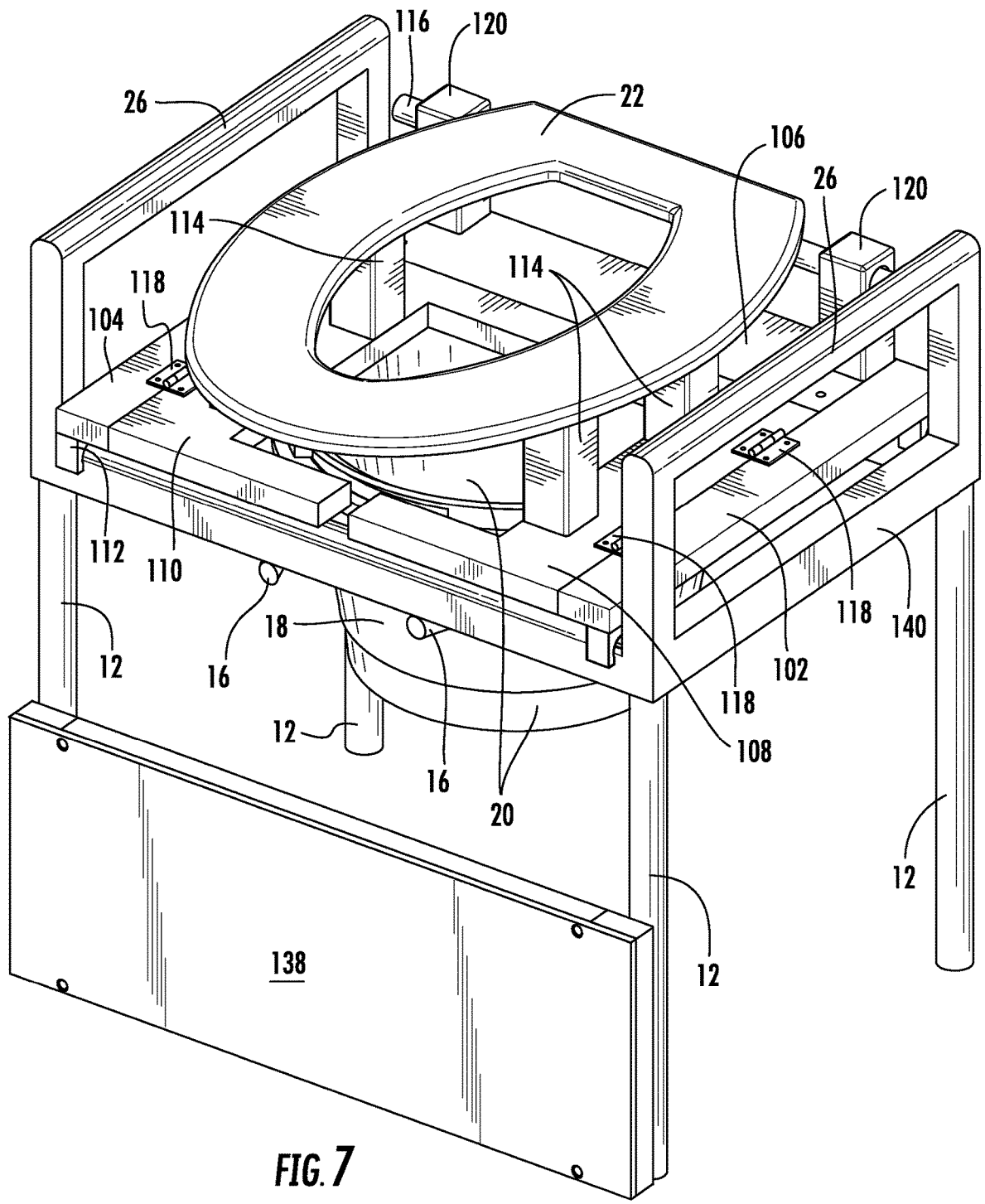
FIG. 7 is a perspective view of a retrofittable commode attachment device of the present disclosure affixed to a commode with a foldable scale/weight shifting sensing pad as part of the system of the present disclosure.
Figure 8:
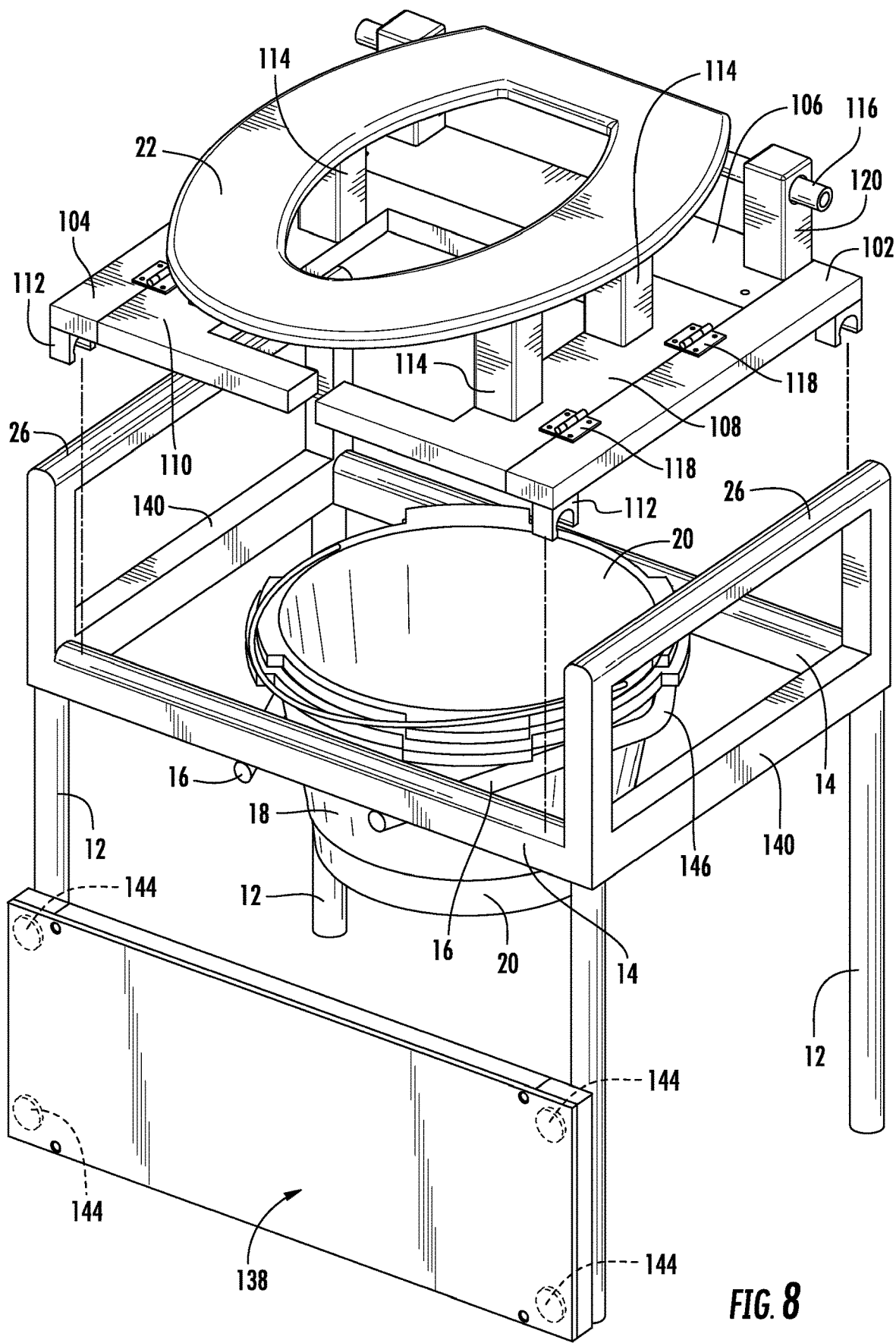
FIG. 8 is an exploded perspective view of a retrofittable commode attachment device of the present disclosure affixed to a commode with a foldable scale/weight shifting sensing pad as part of the system of the present disclosure.
Figure 9:
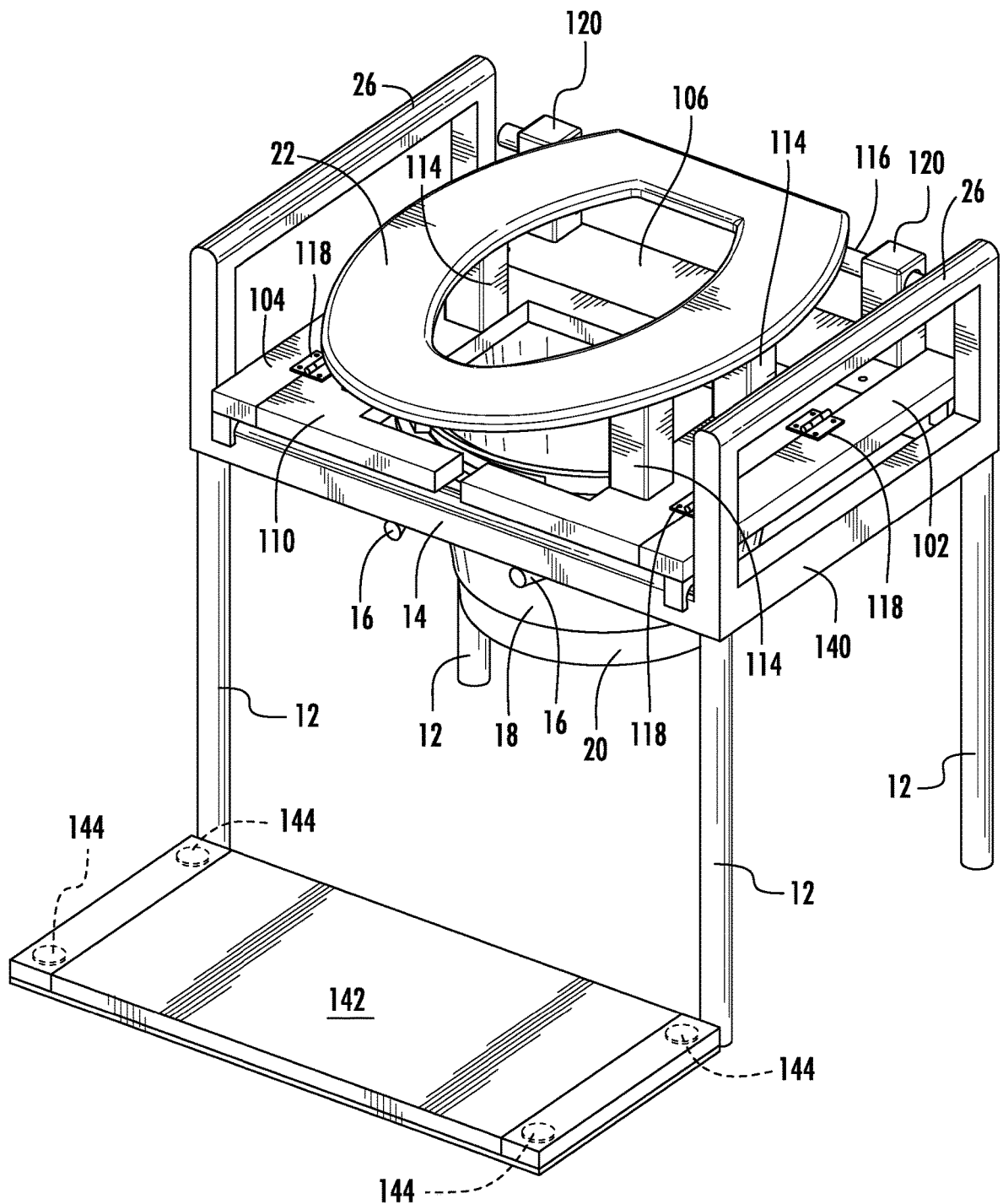
FIG. 9 is a perspective view of a retrofittable commode attachment device of the present disclosure affixed to a commode with a foldable scale/weight shifting sensing pad as part of the system of the present disclosure with the foldable scale/weight shifting sensing pad in the downward and in-use position.
Figure 10:
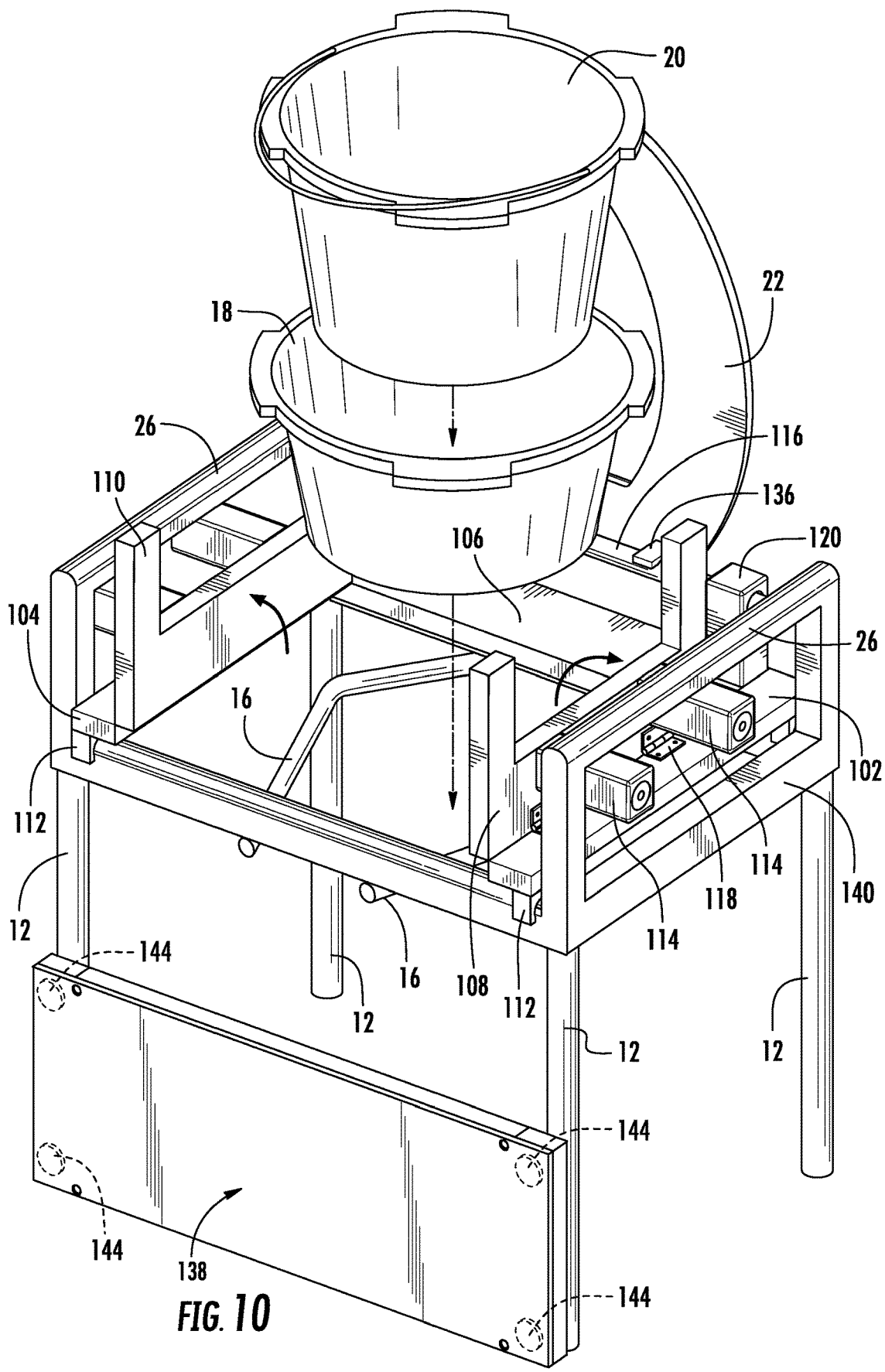
FIG. 10 is an exploded perspective view of a retrofittable commode attachment device of the present disclosure affixed to a commode with a foldable scale/weight shifting sensing pad as part of the system of the present disclosure with the foldable scale/weight shifting sensing pad in the downward and in-use position, but with the retractable side sections of the device in the elevated position to facilitate removal of the bucket of the commode.

The "smart", retrofittable, and portable commode devices of the present disclosure have the ability to travel with the resident from a care facility or their own home to another location where one may use the commode. The seat is constructed to travel with the resident from one part of the facility to the other; travel with the resident when a resident goes home for a holiday; and/or travel with the resident when the resident is admitted to a hospital and they are still required to go to the bathroom on a commode. In order to do so, as shown in FIG. 6, the devices typically have a water tight electrical component compartment 126 within the rear portion of the device that is enclosed by a cover 128 that may be engaged and removed using a fastener system such as a screw or pressure clip or magnetic connection that may be disengaged by prying the cover off. The electrical component compartment typically contains a battery, a controller system that includes a microprocessor that can be a multi-core microprocessor, memory and a local software module that may be an auto-executable application residing within the memory. The electrical compartment further typically includes a wireless or wired data transfer module, typically a wireless data transfer system such as a BLUETOOTH or ultrawide-band wireless transmission system that receives and transmits data from the sensors and systems of the device, including, but not limited to, each of the individual load cells, the camera(s), and/or the microphone(s) used to track the user's health including, but not limited to, the user's weight, mounting profile, dismounting profile, stool quality, urine quantity, urination overall time duration, urination individual stream time duration, urination volume, urination color, stool size (approximated via use of pixel density measured by camera), and defecation struggle based on center of mass movement around the toilet seat of the commode or toilet and nature (stool and/or urination).

In each instance, the commode platform device of the present disclosure allows the resident or user to continue to use the commode and overall system regardless of location to accurately collect and allow the user, a user's authorized family and/or one or more health care providers to monitor that data and proactively respond to changes observed by the inventive devices/systems when the devices compare short term historical data to longer term historical data and an observation of a clinically meaningful health change is observed by the system. The systems used by the health care professionals and/or family are accessed using a computer system that may be any mobile or other computing device. The systems may proactively push alerts of health changes from the unique behaviors of the individuals over time to the family members and/or health care professionals to enable proactive intervention on behalf of the user who may or may not be aware of the changes in their own behavior or health. The comparison of the unique data accumulated over time that includes the amounts and timing of bowel movements, how the user of the device mounts and dismounts a toilet seat and the user's weight over time can each individually and collectively be compared without human involvement or measurement to shorter term, but typically not a single incident data (although this is possible for a fall or gross changes in stool or urine behavior as well). This comparison provides a customized alert to those needing to be alerted to changes in health of the user as well as the user in instances that the user may not even be personally aware of otherwise.

When a senior citizen or other user of the devices/system(s) of the present disclosure uses the system/devices, it is important that the system be constructed to be moveable from one location to another. This may be from one room to another or from one entirely different structure to another where the user may need to use the restroom while ensuring that accurate measurements of urine and bowel movements are made consistently. For example, when a resident is being transferred from the hospital to a care facility, one of the key/vital pieces of information the care facility wants to know is when the individual went to the bathroom last. In the present systems, a seat is assigned to an individual, typically an individual at the hospital who will end up being sent to a rehab center after a procedure or due to age. The objective is to start logging and generating this users profile before they are brought to the care facility. This would allow the system to generate a user's normal behavior profile sooner and give the care facility nurses a better idea of the individual's bowel functionality. Presently, health care professionals have to guess and generate their own assessment. When using the systems of the present disclosure, the system lets the health care professionals know exactly what is happening with that resident post hospital treatment. The present disclosed solution helps care facilities avoid re-admission fines because real, consistent, and accurate data is captured that can tell if a re-admission was avoidable or unavoidable.

Additionally, it is possible to proactively use the systems of the present disclosure prior to old age or a surgical event to establish a baseline of information and identify when a changed condition occurs that might suggest that the user should seek medical care on their own proactively before a medical condition worsens. Regardless of when the system(s)/device(s) of the present disclosure are employed in the lifetime of the user, the system is able to essentially calibrate long term "typical" use of the various factors it measures and compare the data over a shorter period of time in order to alert the user of changes in health that are evidenced by the changes in the data collected by the system. For example, a short term observable health care concern may be a single incident of diarrhea or shortage of urine volume and/or duration.

The presently proposed "smart" commode platform has the ability to be powered in at least two different ways. Power is typically provided to the commode of the system either by Power over Ethernet (PoE), which would more typically be used in the case of a fixed toilet seat location or a fixed commode location, or by a battery or batteries, which would more typically be use in the case of a commode which is generally preferred to be portable. The battery may be an alkaline or a rechargeable battery. Depending on the battery size used in the system there is a possibility that the commode might operate in two different capacities based on the power requirements of the system. If a microcontroller and processor 132 used in the device requires a lot of power, the system may have to run a lighter version of the software program to maintain battery life. The battery operated version allows for the easy transfer of the toilet from one location to another depending on the residents situation. As such, a battery powered solution is typically preferred, but not necessary.

Figure 14:
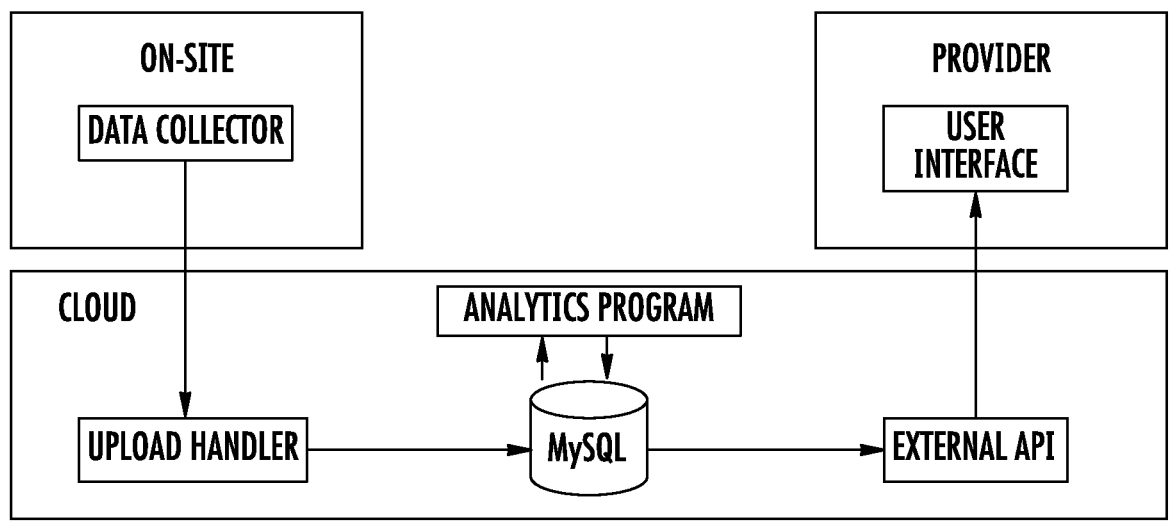
FIG. 14 is a schematic layout of a computer server and data communication system according to an aspect of the present disclosure.

The retrofittable commode systems of the present disclosure will utilize one or more of a variety of sensors that include: load cells, microphone, and camera. The commode systems/devices of the present disclosure will collect and log the data and, as shown in FIG. 14, the data can be transferred to one or more cloud based computer server systems for storage and/or processing of the data. Analytics may be run either on the device itself, but more typically within the cloud or other server based system that receives the data from the various devices. The data is typically transmitted to the cloud based server systems in realtime or approximately realtime to enable faster alerts to be sent to health care professionals, family members of the user and/or the user. An external facing API may be employed to allow other authorized parties to access the data collected either on a collective or individual basis, but in accordance with relevant privacy and health care policies and laws when this is offered. The API may be only accessible by the overall system administrator of all devices and locations to limit access to data. The system's data may be accessed via a secure website or dedicated program that interacts with and processes the data on the remote server. An exemplary graphical user interface of the computer system used by the user is shown in FIGS. 16-21.

With the commode devices of the present disclosure, the existing seat on the commode may be retrofitted to include the sensors and devices of the present disclosure or these may be provided with the purchase of a new commode. Installing the necessary sensors onto an existing commode facilitates lowering of costs and allows users to retrofit existing commodes instead of purchasing a new one. With the load cells 144 and other sensors, the presently proposed commode attachment will perform untethered bowel and bladder charting in a consistent manner regardless of the user's location because the commode and device are portable. The commode attachment and systems of the present disclosure provides evidence to Medicare/Medicaid to help facilities prove they are not at fault for recurring hospital visits.

If a resident/user goes to a care facility and after a period of time of care they are prompted to leave because Medicare or their insurance only pays for a certain period of time and that time has passed, residents may leave the care facility before they are ready to do so in their care. When these residents go home these residents may have a re-admission to a care facility. When a resident goes back for a re-admission both the hospital and the care facilities typically get fined. The commode of the present disclosure has the ability to follow a resident wherever they go especially when they have not successfully completed a bowel and bladder training program. Being able to maintain an accurate record of a resident's bathroom habits is critical. As discussed previously, discontinuity in care and inconsistent charting of a resident's bowel and bladder activities leads to missed signs of emerging health issues. The systems and devices of the present disclosure provide doctors/nurses/telehealth providers/family members/residents/users with a history of a resident's bathroom behavior. This bathroom data alongside the electronic health record (EHR) system records allows doctors to better diagnose a patient they have not seen before and even do so from a location remote from the user/resident in an accurate and meaningful way and also allow for health professionals from anywhere in the world remote from the resident or user to be alerted to health and behavioral changes observed by the data recorded by the systems and devices of the present disclosure.

Currently doctors send residents to the emergency room (ER) because they do not have enough information to treat or diagnose the resident/patient. The systems and devices of the present disclosure keep and record individualized health data for a variety of health indicators, summarizes and uses artificial intelligence to analyze the data to provide medical professionals with a tool that will help eliminate unnecessary ER visits. In the case of the present disclosure, data is observed to provide timely diagnosis by observing deviations from trends in data while generally not actually testing urine or stool for physical properties using a laboratory-type testing method. Laboratory-type testing is avoided using the systems and devices of the present disclosure and the systems/devices of the present disclosure are typically free of any laboratory analysis system to analyze the urine or stool. This means a doctor essentially anywhere in the world can identify a treatment over the phone or they can treat the resident long enough to send them to their primary care doctor.

The commode devices of the present disclosure typically include load cells 144 under the seating surface of the commode. The load cells 144 function to capture the full body weight of a user. In addition to the commode's load cells 144, the system often includes a detachable foot scale. The detachable foot scale may be in the form of a pad 138 (FIGS. 7-10, 12) or may be a construction similar to the foot supports on a wheelchair (see FIG. 11). In the case of the pad 138, the pad is typically hingedly or otherwise rotatably connected to the legs of the commode to allow a user to easily lift and lower the pad from a horizontal position to a vertical position by hand and without the use of tools. Conceivably, a slow lowering feature may be employed within the hinge system so that the pad does not forcefully fall into the horizontal position when the user moves the pad from the vertical position to the horizontal position, in particular. The force of gravity may cause harm over time to the attachment in such a case. This is especially true in the case of the elderly population, which may not be able to readily bend and hold the weight of the pad throughout the lowering of the pad. A hydraulic or pneumatic system may be employed to help with the lowering of the pad. The pad 138 has a front surface and a back surface when in the vertical position. The back surface is the weight bearing surface 142 that the user would stand on when mounting or dismounting the commode. The pad will typically have a load cell 144 in each corner or corner section of the pad 138 to measure the force at each corner and record not only the weight of the user, but also the manner in which the person mounts and dismounts the commode's seat.

The retrofittable toilet or commode attachment devices of the present disclosure may use "soft close" technology for all of the moving parts including the device itself and the toilet seat. Soft Close hinges come in many formats. Models for devices of the present disclosure, a toilet seat and/or the lid typically use a combination of a spring and a friction washer, so that as you lower the seat/device, the friction washer slows down the descent, while at the very end the spring compresses slightly to provide a very gentle impact on the toilet bowl or other surface.

Figure 11:
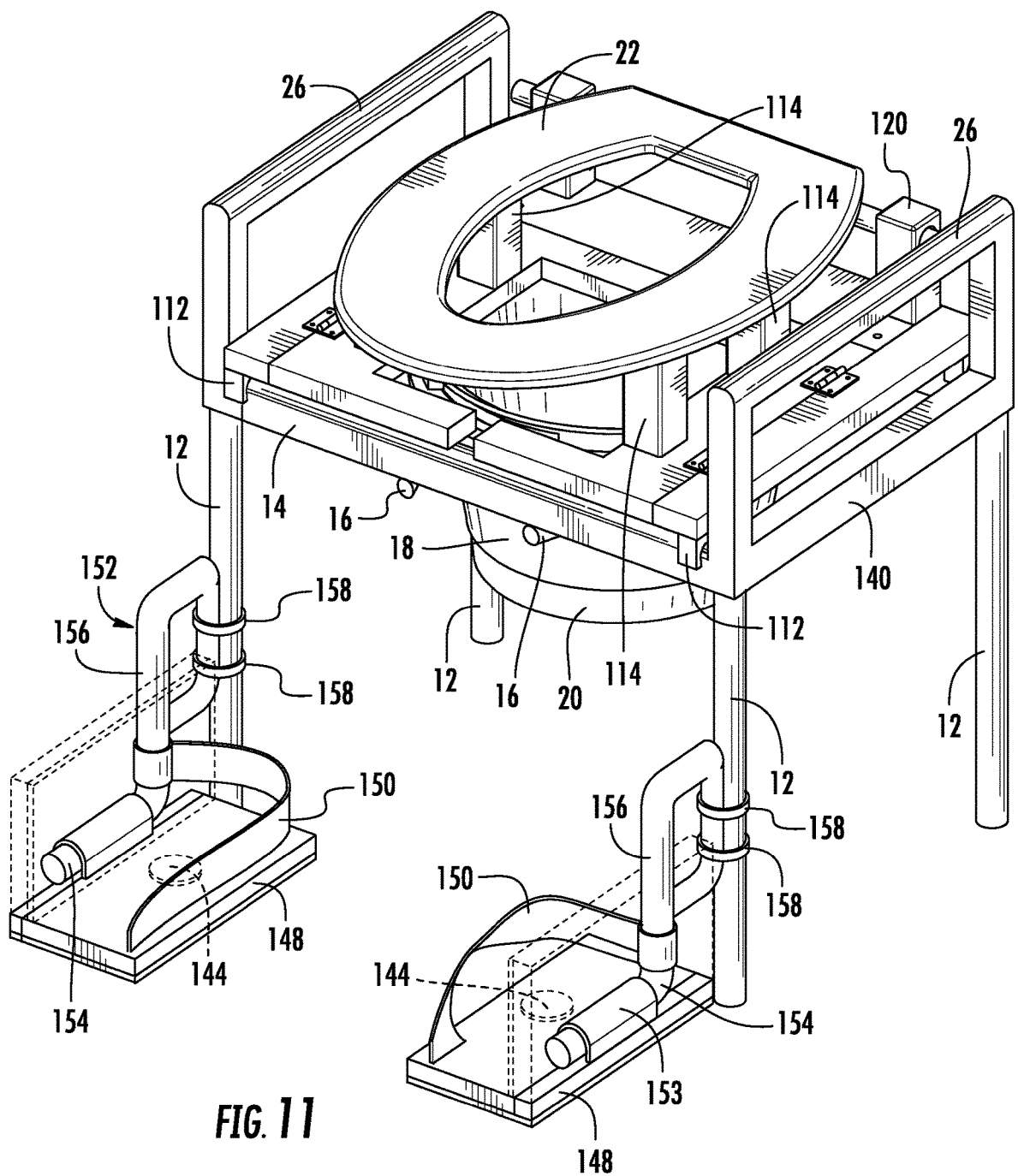
FIG. 11 is a perspective view of a retrofittable commode attachment device of the present disclosure affixed to a commode with a foldable scale/weight shifting sensing pad for each food used as part of the system of the present disclosure.
Figure 12:
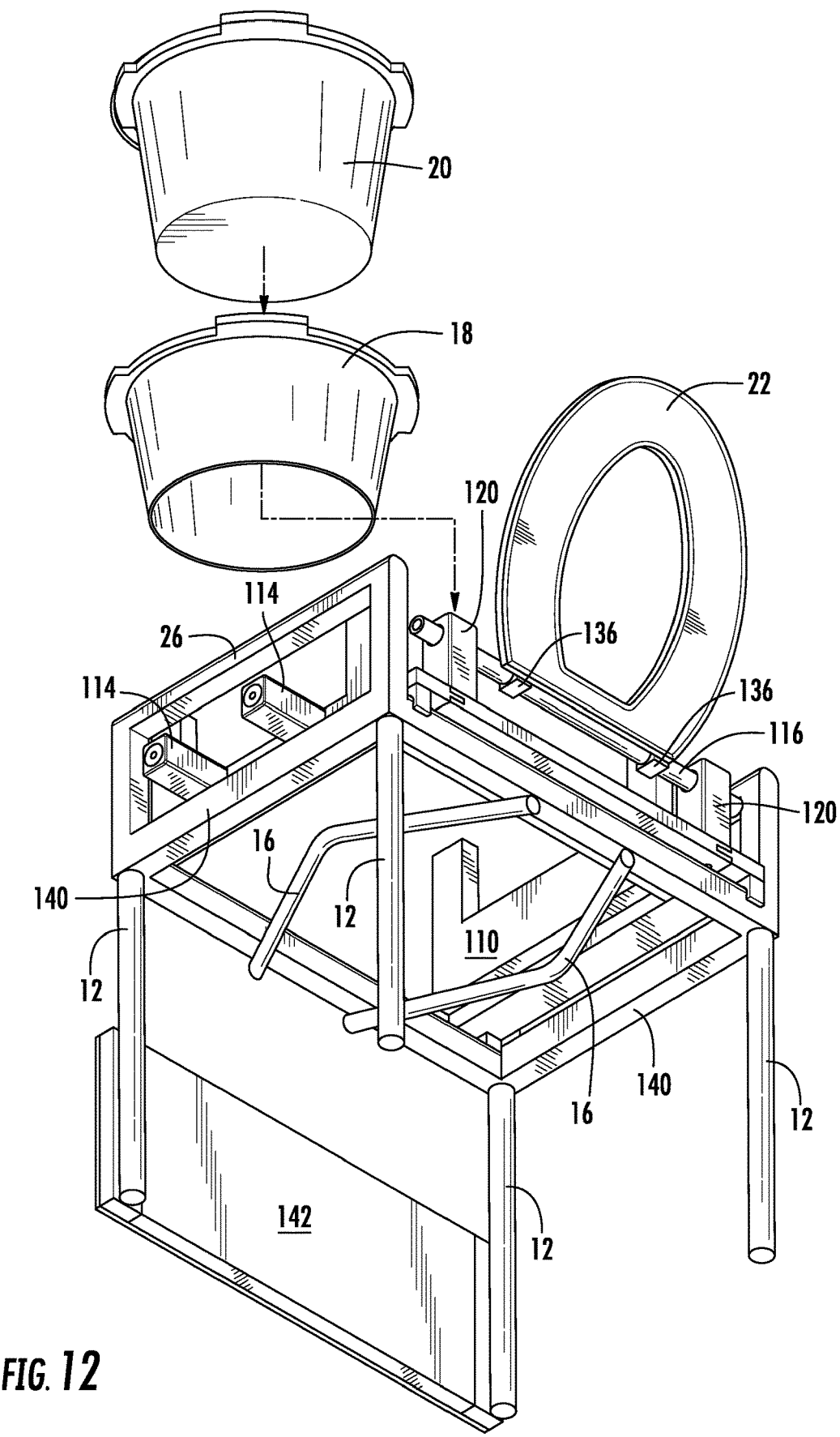
FIG. 12 is a bottom partially exploded perspective view of a retrofittable commode attachment device of the present disclosure affixed to a commode with a foldable scale/weight shifting sensing pad as part of the system of the present disclosure.

As shown in FIG. 11, when the individual foot scales 148 are employed they typically would have a small platform that is attached to the leg of the commode and can swivel back and forth from a horizontal to a vertical position as well. In the case of the individual foot platforms, a single load cell 144 is typically spaced within each foot scale. Each platform will include a single load cell that will record and account for the pressure/weight of the users leg. The rest of the user's weight from the waist up is accounted for from the toilet seat load cells, but the load cells within the pad/scale 138 or foot scales 148 can also conceivable measure overall weight as the user mounts or dismounts the commode's seat, but further also records individual data about the weight on each foot as the user mounts or dismounts the seat. This is also done by the toilet seat load cells and collectively provide a mounting and dismounting force behavioral model over time. The foot pad scale load cell data is not absolutely necessary for this measurement, but provides an even more detailed analysis of typical behavior for mounting and dismounting as one stands and lowers or raises oneself onto and off the toilet seat as opposed to just which side or area of a person's buttocks applies force to the seat as the person is lowered onto the seat and the alleviated forces when the person's buttocks leaves engagement of the toilet seat. The foot scales 148 typically have foot straps 150, but these are optional, and have a foot pedal support engagement channel 153 that receives the horizontal foot pedal engagement section. A loop section 156 is also typically employed and engaged to the front leg 12 of the commode using one or a plurality of straps 158.

Since seniors are habitual they tend to follow a schedule. As a result, most residents in nursing homes are trained to keep their body on a schedule to help maintain continence. Since they are on this pattern, the systems/device of the present disclosure using the data from the various load cells can compare the user's strength, gait, and mobility and determine, over time, if the user's gait is affected by a health issue and/or through fatigue throughout the day. Knowing how the user's gait is affected as the day starts or ends may be used to help prevent future falls and instruct care staff to provide assistance later in the day for certain individuals in need thereof.

Additionally, one or a plurality of load cells, typically a single load cell positioned in the center of the bucket, would be used to capture and measure the weight of the commode bucket. Comparing time stamped images to the same time stamped load cell data (weight captured from under the bucket) will facilitate a determination of the weight of the urine and/or feces that comes out of the user/patient. The system can then convert the weight of the urine to volume in milliliters. This will help the systems of the present disclosure not only identify if a resident is dehydrated, but it will also allow for an understanding of the size of the user's bowel and bladder. Essentially an accurate estimated volume of a user's bladder evacuation in each instance and an overall accurate estimated volume of the user's bladder itself can be estimated over time.

Based on the force the load cell under the bucket sees the system is also able to calculate and identify the velocity of the urine coming out. Urine velocity is determined using a combination of the audio frequency during urination, the length of urination, and the change in weight of the load cell in the bucket. Urine velocity helps provide an understanding of the health of the user's bladder. As a user urinates and defecates, the devices and overall systems of the present disclosure are able to convert the weight of urine and the weight of stool to an output volume. The systems of the present disclosure are also able to use the bucket weight data to help assist the computer vision camera(s) 124 and the microphone(s) 122 to better estimate urine and stool output volume. The systems of the present disclosure may do a comparison of the urine and stool output and compare one day's total to the past seven (7) day average, for example. The systems of the present disclosure may compare each bathroom time slot to the previous time slots. In the case of a bowel and bladder training program, a resident will be prompted to void at specific time slots each day to train their body to void at approximately the same time each day thus helping complete a bowel and bladder training program. This consistency of voiding at the same time trains the user's/resident's body to be continent. For example, Mrs. Smith is prompted to void every two hours starting at 8 am.

So there would be an 8 am time slot, a 10 am time slot, etc. The systems typically are configured to compare and capable of comparing the previous data to generate a trend. Using this information/data the systems of the present disclosure can start identifying early indicators that the body is changing for the good or for the bad.

In addition to using load cells to help provide a variety of data, the systems of the present disclosure capture a comfort profile. To do so, the systems as discussed previously typically utilize four load cells under the seat to map the body movement or the change in the center of mass for the individual during the entire time the commode of the present disclosure is in use. The system monitors the load on each of the load cells and compares their movements at key events of the bathroom visit by comparing the data at the same time stamps. Key events that can be measured include when a resident starts to void stool or urinate, when a user is passing gas, and when the user first sits down on the seat or gets up off the seat.

By way of example, when a resident starts to urinate the systems of the present disclosure looks at how their body position changes and can observe if the user rocks back and forth, lean to one side, or any other movements while the user is seated on the commode/toilet seat. The system/device can also look at the urination intervals. If for some reason the urination stream of the individual stops then starts again the systems/devices will look at their body movement to help determine if there was any sort of discomfort or not. This is a significant feature since seniors and humans generally rarely complain, especially when it comes to their bathroom habits, typically out of a sense of embarrassment.

When a resident starts to defecate the systems of the present disclosure are capable of looking at how a person moves or shifts when using the commode/systems of the present disclosure. The systems of the present disclosure are typically sensitive enough to be able to detect a user's movement, a user shifting his/her weight, or a changed center of mass of the user on the seat during the time leading up to the defecation, during defecation, and after defecation. The system can even track the time in between each of these events and track habits. The systems are able to examine/compare how a user's body acts after each piece of stool is passed. Additionally, the systems of the present disclosure are able to determine if a user pushes their muscles too hard or in general had a hard time passing stool, the resident is at risk of getting light headed or experience some form of weakness, and as a result residents are at an increased risk of falling. Based on data able to be collected and analyzed, the systems of the present disclosure can alert a family member, a nurse or other health professional to limit the user's mobility to reduce the risk of falling.

The systems of the present disclosure are typically able to look at the user's body movements during key events that will help create a personalized understanding/profile of whether or not the user is in distress and/or whether or not the user is aware of the distress. Often patients, who are often long term care facility residents or just seniors will not complain or alert doctors or family members when they feel unhealthy or just "off". By looking at their movement during these events the system is able to alert a user, a family member of the user and/or a health professional if there is a problem the user may be having but hiding or simply not informing anyone of as it occurs. By developing a "normal" profile of a user's movements over a longer period of time than a shorter period of time proximate present day, the system is able to figure out when a body starts to strain. This profile forms a baseline model of how the user acts and then determine if a more recently observed behavior is atypical or somehow "off" from the user's typical behavior. More importantly, solutions relying on human observation in care facilities have no chance to provide proactive care, which is a major benefit of the present systems. Other systems are only able to provide reactive care and often rely on limited subjective data. The present systems are able to dynamically examine more than a single event/use and are able to look at and compare a single use or a series of a few recent uses and compare that to an overall trend, which is measured over a period of time longer than the series of a few recent uses to determine if there are any potential concerns that may require further medical investigation. Based on this information, the medical professional and/or family member may be alerted via a mobile application or text or SMS or other messaging to them typically over a wireless or wired communication network. Alerts can also be sent to nurses having direct care responsibility for the user when a "significant downwards trend" of behavior or health is observed.

In addition to how a person behaves while seated on the commode of the present disclosure, as discussed above, the systems of the present disclosure are able to establish a "Mount/Dismount Profile," which is basically the pattern of how the user initially sits on the toilet/commode seat and how the user stands up after use. The systems of the present disclosure are able to determine and record how the user is transferred/mounted on the toilet. The systems look at the user's body movement when they initially sit down. One significant feature is that the system is able to notify a family member or healthcare professional whether the user sat or was transferred by a CNA too hard onto the seat. If the force peaks above a certain threshold when the user first sits on the toilet, the systems transmits an alert signal, typically a wireless signal via a global computer network to a family member and/or a Charge Nurse or other health care professional that the transfer was too rough or there may be an injury or other issue occurring. This feature ensures that proper training and supervision can be implemented. These "hard" transfers are a real problem in long term care facilities and hospitals. If the systems of the present disclosure detect a hard transfer the head nurse in charge in a care facility should be informed of this fact. There are at least two reasons why the present systems provide an alert such as this. The first reason is because the resident might experience bruising/discomfort after that should be addressed as soon as possible. The second reason is to make sure the CNA or other health professional or person who performed the hard transfer gets re-trained on how to do it better.

In addition to monitoring the force and pattern of how a person mounts the seat of the present system, as discussed above, the system also is able to measure and track the force and pattern of how a user dismounts off the toilet. The system sees how a user lifts their body up off of the toilet/commode. When used, in addition to or instead of the load cells on the device under the toilet seat of the toilet or commode, the load cells 144 of the pad 138 or foot scale 148 look at how the person distributes their body weight as they stand up. The system tracks and records how the user stands including which foot they put more weight on and for how long and with what force. The system also looks at how their body is balanced when they stand up off of the foot scale. Additionally, the systems and devices of the present disclosure record the data and analyze how the person's balance changes over various lengths of time, including over the span of a day, a few days, weeks, months or even years. Looking at how the balance changes not only throughout the day but from day to day is extremely useful. This data has the potential to help prevent falls and other potentially harmful events. The pad 138 and the foot scale 148 may operate in a manner similar to how a Dr. Scholl's kiosk measures or other similar system that measures the entire force footprint across the entirety of the bottom of a person's foot or feet. The systems of the present disclosure are typically capable of looking at/recording and tracking historically exactly how the user puts pressure on their feet as they stand up from going to the bathroom. Over time, the systems of the present disclosure are able to look at a user's gait as the day goes on. It is normal for a senior/older user to get tired as the day goes on. By looking at how an older person stands up after sitting down on the toilet seat, this information provides an indication of how balanced the user is and the system can proactively alert nurses if a user may need assistance with mobility throughout the day or perhaps only later in the day. This provides the user with a sense of independence and only assistance when assistance is actually needed based on data actually collected and unique to the user. The systems of the present disclosure are able to look at how fast/the acceleration of when the user lifts up off the toilet and put all body weight on their feet. The system does this by measuring how fast the weight changed over a specific period of time across some or all of the load sensors present in the seat and the foot pedals. This feature will help determine a user's mobility and if the user may have fallen off of the toilet or if they just stood up.

In addition to load sensors 144, the commode seat device and systems of the present disclosure typically also include at least one microphone or a plurality of microphones 122. The microphone(s) 122 assist in creating a custom urination profile. The system uses a microphone or microphones 122 to capture the sound frequencies inside of the toilet bowl. Once the systems of the present disclosure receive the sound signal file, the cloud based analysis system server/software filters out the ambient noise and looks for the sound frequencies that resemble urination, defecation, and passing gas. The software of the present systems are able to identify and label what is going on inside the toilet bowl based on the data received by the microphone(s) 122. This allows the system to identify the user's urination profile, volume of urine (in conjunction with the bucket load sensor(s) as discussed above), and if they are passing gas or stool. The systems of the present disclosure are able to look at how many urination intervals a user has during each bathroom visit as well as the length of time of each urination.

During a single bathroom event a user "normally" has one continuous urine stream, or single interval. But when a user isn't feeling well or something is wrong, they might stop and start their stream several times. This is also recorded and measured. The increased amount of "intervals" are a direct indicator that a user is having a hard time voiding. That said, if a user normally voids in multiple intervals then the systems compares the length and number of intervals against a length of time average, which is typically a seven (7) day average, a thirty day average, or within a certain predetermined time period. The system then is able to determine if the user's behavior is consistent or not with the user's own unique prior behavior profile. The system is able to normalize the abnormal and identify when the abnormal pattern that is normal for the individual user has abnormalities itself. During each visit, the systems of the present disclosure sense and record data received from the microphone(s) that includes the urination duration and duration of each interval. The systems of the present disclosure are able to see how long a user normally spends to void his/her whole bladder, compare time, compare volume, compare intervals, and compare velocity of voiding urine at each instance.

In addition, the systems of the present disclosure are able to look at the time from when a user sits down to the time that the user starts to urinate. Since seniors are habitual, they tend to repeat the bathroom routine daily. Knowing this, we are able to analyze the time it takes for a user to start urinating and how long they should be urinating. If there is a delay in urinating and the bathroom event runs longer, this may or may not be a problem. The increase of visit duration could be a direct result of a user having trouble urinating or it could mean more such as constipation or a urinary tract infection. Systems of the present disclosure also look at the time differences between each urination interval. If a user does void their urine in multiple intervals then we will look to get an average interval time and compare the user's interval time to see if there is a large enough discrepancy that the bowel & bladder nurse needs to check out. We will also try to compare the volume of urine expended during each interval and check if it's with normal parameters or if something is different.

In addition to urine detection, the systems of the present disclosure also are able to measure and detect and record audio/video of the stool when a bowel movement occurs. The camera or cameras do not typically have visibility or are otherwise directed toward or aimed at the user's anus. To accomplish this, the commodes of the present disclosure typically have one or more camera 124 that is able to view the stool both as it is leaving a person's anus and within the commode or toilet. This allows the systems to be able to measure the quality and quantity of the stool sample in real time as it occurs. The stool classification is able to be made by the systems of the present disclosure. The system can automatically grade/analyze the stool on the Bristol stool chart. The Bristol stool scale is a diagnostic medical tool designed to classify the form of human feces into seven categories. The seven types of stool are: type 1, which is separate hard lumps, like nuts (difficult to pass and can be black); type 2, which is Sausage-shaped, but lumpy; type 3, which is like a sausage but with cracks on its surface (can be black); type 4, which is like a sausage or snake, smooth and soft (average stool); type 5, which is soft blobs with clear cut edges; type 6, which is fluffy pieces with ragged edges, a mushy stool (diarrhea); and type 7: Watery, which is no solid pieces, entirely liquid (diarrhea). The automatic grading is done by using a camera that is typically mounted on the back of the toilet within the housing 121, but could be placed anywhere where the entirety of the toilet bowl is viewable including the side of the underside of the devices as shown in FIG. 4. Housing 121 may be an enclosure with the camera(s) and/or microphones, which can be standard or directional microphones, being the only structure with consistent visibility outside the housing. The housing 121 may also be a partial enclosure that is open or at least partially open such that it functions as a shield over the top of the camera(s) and microphone(s) to essentially make the components invisible to the user of the device when viewed from above. In the case of the embodiment shown in FIG. 15, the housing has a curved portion 123 that is typically pliable (typically repeatedly deformable by the force of a user using his or her hands without the use of tools) and extends from the back of the retrofittable commode device and then has a planar or at least generally planar section 125 that typically incorporates the camera(s) and/or the microphone(s). The camera(s) and microphone(s) are typically angled downward such that they readily view the contents of the toilet and are typically either covered or designed to be flush with the housing's planar section. This facilitates easy cleaning. Additionally, the curved section 123 may be constructed of a material that is moveable, but retains its position when left unaltered by the user or other person or the housing may be moveably connected to the back portion of the device such that a user may adjust the angle of the camera(s) and/or microphone(s) by simply pulling or pushing the housing. An adjustment fastener, which may be a set screw or other fastener, may be used to apply a force to the housing and hold it in place once it is set in the correct position for viewing the toilet bowel. The camera(s) 124 takes images and/or video footage of the bowel and may process the images and video. The systems use the computer vision algorithm and machine learning to identify the stool type. The system is able to identify if there is blood in the stool as well as the approximate size/weight of the stool using pixel density. Urine can also be classified using the camera, which can determine the color and degree of yellow in the urine and whether the color indicates that there is blood in the urine or not. This information will allow the systems of the present disclosure to determine a level of dehydration/hydration of the user who urinated.

The systems of the present disclosure/invention employ a software element on a local computer system and/or on a cloud based server that is in signal communication with a user's device via a network such as a global server network (the internet) as well that works with local and cloud based databases and processor systems to collect data when in normal use and when the commode or toilet seat is transported to a remote location that is not the typically used location for the commode. The data collected will be secured according to HIPAA standards and may be sorted and/or analyzed aggregately as well as based on the individual user. If the seat is taken out of the care facility/home to another location, such as to a loved one's home, a mobile app as part of the systems of the present disclosure will function to remind the loved ones or those in care of the person using the system (if needed) to keep the resident on a consistent bowel and bladder training program and prompt the resident/user to void on the scheduled time. The bowel and bladder training program will be exactly the same for home use as for facility use. Based on the user's training program the systems of the present disclosure will let nurses and/or family members know when the user needs to void their bladder in particular, but also their bowels. This promotes continence and independence of the user.

While not preferred, depending on a care facilities budget constraints, some facilities might take a sharing approach when it comes to the smart commode device of the present disclosure where more than one user can share the devices with one user using the device at a time. If care facilities want to share one or more smart commodes between a plurality of residents the system will be able to assign and log the bathroom data to the right user, typically accomplished by login or other identification such as user face identification or fingerprint identification or other similar unique identification system spaced on the device itself or conceivably a mobile device operably linked to the commode devices of the present disclosure such that a user can log into a mobile application on a smartphone or tablet computer system and use that system's authentication to register the appropriate user. This can also be done using a dedicated mobile software application that can also optionally display the data from the device/systems of the present invention to the user.

Since the devices of the present disclosure might even be shared with more users, an interface for the CNA or nursing staff or other health professional to enter the ID of the resident before the resident gets off the commode may also be employed or employed instead of another user-based login. If the resident gets off the commode before an ID has been entered, the commode will send a real-time notification to the health professional's dashboard. There will also typically be an audible and/or visual alarm associate with such an event where the user has not been identified by the user prior to use. A notification chime similar to the sound indicator that occurs when you're not wearing your seatbelt may also be employed to ensure the nurse/user/family member tags the bathroom data to the right resident/user. This could be done via a mobile application or a hardwired keypad/touch screen located on the commode.

The systems of the present disclosure typically employ a mobile application that can be used on a mobile computing device that has at least a display, which is typically a touch sensitive display, a user input device such as a mouse may also be used or instead of a touch sensitive display and processor. The mobile application may be used by health professionals and/or family members of the user of the commode or smart toilet seat employing the features of the present invention. The mobile application will also typically enable, prompt and regulate a user's Bowel and Bladder training program. A Bluetooth or other wireless communication system may be used to allow loved ones of the user or a health professional to connect the mobile device with the device (commode or toilet seat) of the present disclosure to enable the controller or mobile application to retrieve data securely.

Regarding the overall physical commode device itself, it is an all in one platform that uses clips 112 that snap right onto the frame. The commode typically uses four pressure fit snaps to attach the platform to the frame of the commode.

The platform of the seat of the present disclosure will have a fixed base. Once attached to the frame, there will be a lock or set screw that will keep the platform from shifting on the frame. Load cells 144 are mounted on standoffs to keep seat level and to capture the users total body weight and movement as discussed above. A detachable and swivel foot scale 148 or pad scale platform 138 is also typically employed. When employed it is conceivable that a separate data signal transmitter may also be employed in association with or incorporated into each of the load cells of the present disclosure to allow the load cells to transmit their data to the controller within the electrical component compartment and then to the database server remote from the commode system for storage and analysis. Alternatively and more typically, the load cells will be signal linked with the electrical compartment and ultimately the data storage server via a wired connection either embodied within the plastic components when they are produced or affixed to a surface, typically a surface not readily visible to the user and extending from the load cells to the electrical component compartment. The scale systems of the present disclosure will attach to the front right and left of the commode frame. Each pedal of the foot pedal weight scale 148 is typically able to swivel like a wheelchair footrest. As discussed above, each of these footrests will typically have a pressure sensor on it to enable the system to capture a user's full body weight and measure forces upon mounting and dismounting the commode or toilet seat.

The electrical component compartment 126 can be separately mounted to the platform located on the back of the commode instead of incorporated into the device as discussed above. As discussed above, the controls will have Wi-Fi or other wireless signal to send the data to the care facilities network. If a user takes the retrofittable commode device or a commode having the device attached to it home for use at home, the device is able to connect to a phone or to another wireless network system to continue to automatically send data, typically in realtime, to the appropriate data collection server. The systems of the present disclosure will have the ability to function on two different power sources. The smart commode can be hardwired to the wall and/or powered over Ethernet (POE) and/or have a place to plug in a battery, essentially making a mobile/untethered bowel and bladder system. The load cells 144 may be either affixed to the outside surface of a toilet seat to be used in connection with a typical toilet seat or the commodes of the present disclosure or built into the interior of the seat.

Figure 15:
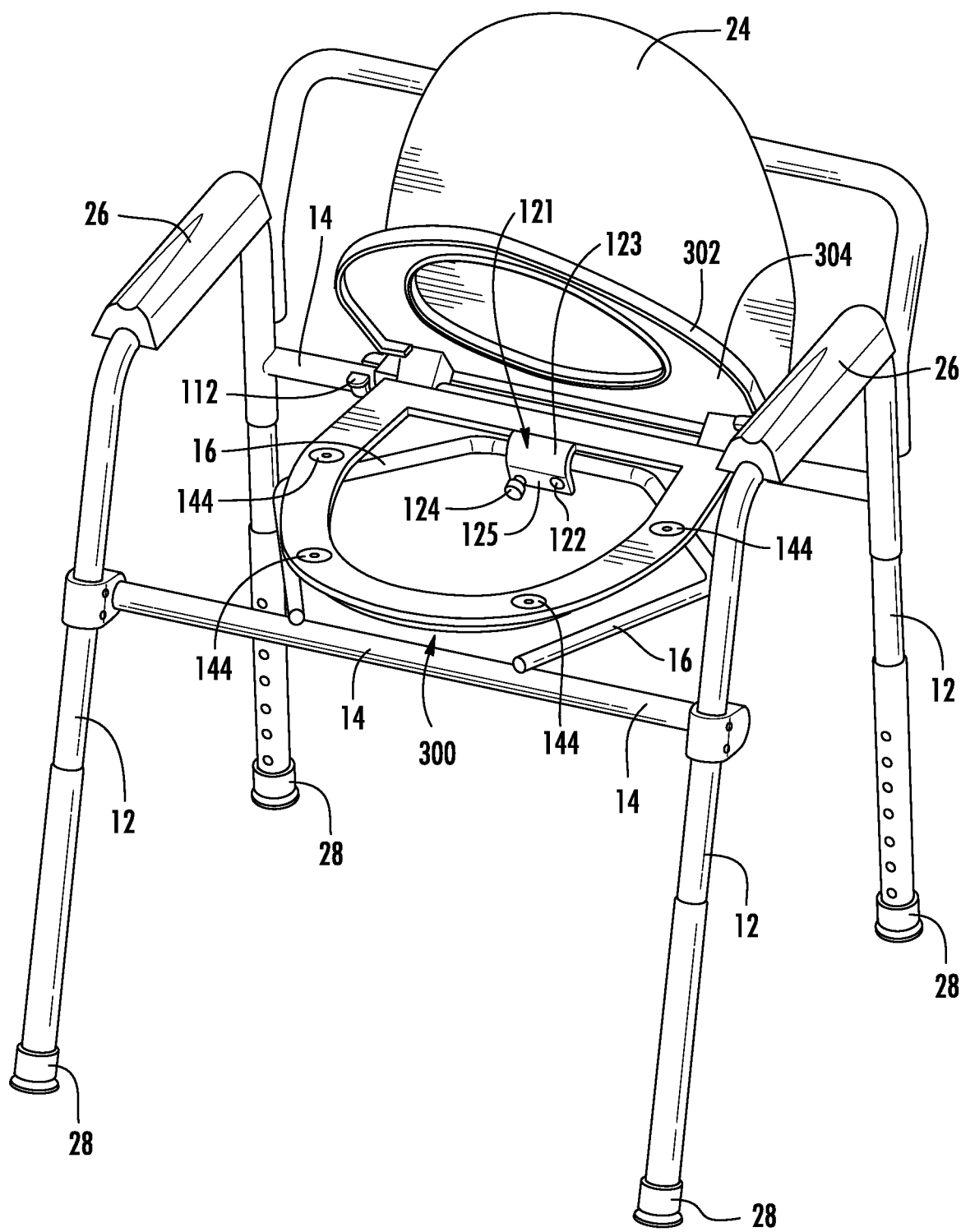
FIG. 15 is a perspective view of another aspect of the present disclosure where the retrofittable commode attachment device is a system configured to be placed under the toilet seat of the commode or under the toilet seat of a traditional toilet and is rotatable in and out of a "use" position similar to the standard toilet seat and lid, when used, of the commode or typical toilet.
Figure 16:
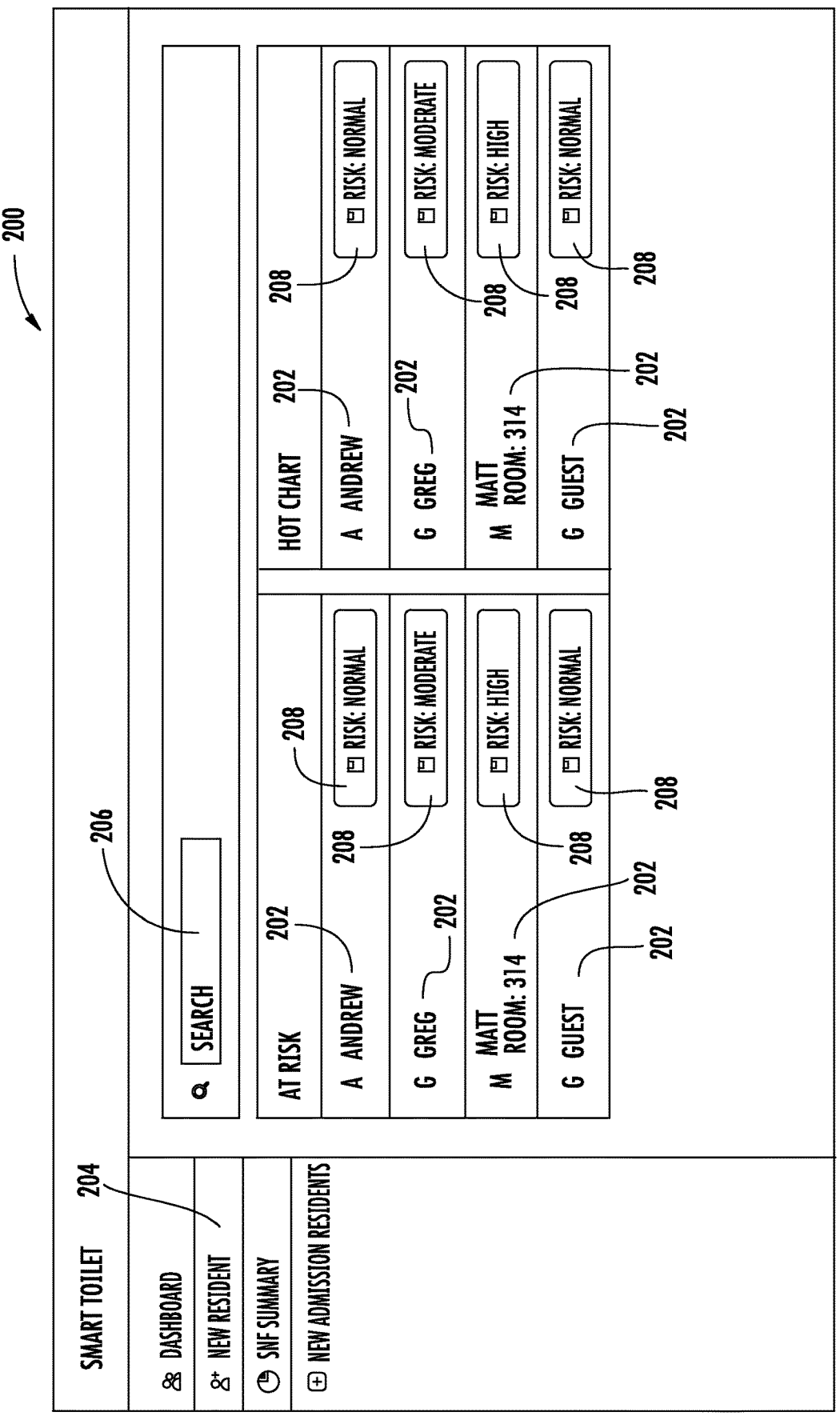
FIG. 16 is an exemplary user dashboard view of a graphical user interface for the systems of the present disclosure to convey single data points, sensor readings and artificial intelligence and analytical data alerts to the user.

In another embodiment the retrofittable commode device may be used as an added component that may be retrofitted not only to a commode, but also the device could be used with a toilet seat in certain embodiments as well. For example, when the retrofit smart commode device is constructed in a manner like that shown in FIG. 15, the device 300 is a generally D-shaped or toilet seat shape, but designed to matingly engage the underside of a toilet seat 22 having a downwardly extending perimeter lip 302 that define at least a portion of a device receiving cavity 304 on the bottom surface of the toilet seat 22. The system conceivably be fixedly engaged with the underside of the toilet seat whether or not there is a specifically designed toilet seat of the present disclosure having a device receiving cavity, but that is not typically preferred because that may change the ability of the seat to properly be level when one uses the seat. The device as shown in FIG. 15, the system may be snapped into engagement with the very same rear horizontal support 14 that already exists on the commode. The device is rotatably engaged such that it can move up and down along with or independently from the toilet seat and lid. There is a back bracket that extends downward from the back portion of the device and contains the microphone 122 and camera 124. As with other embodiments where a camera may be employed, the camera may include and typically does includes a light emitting diode or other light source that illuminates the interior of the toilet bowl.

In addition to the device itself, the systems of the present disclosure utilizes a software system (see FIGS. 16-21) and the system typically goes through both a detection phase, a diagnosis phase, and a correction phase. The detection phase is where the commode or toilet seat retrofit device identifies slight deviations in the user's behavior that could lead to a potential health issue. The device will build a resident-specific behavioral profile through computer learning. The sensor(s) and camera(s) will not only be able to detect strong abnormalities such as diarrhea or urinary tract infections, but also more subtle differences such as constipation or chronic and acute renal failure. A comfort matrix will be able to detect weight shifts that may be indicative of pain or discomfort during a bowel movement. An algorithm will also look at the consistency of bowel movements during the day and how many times they use the restroom. The commode or toilet seat devices of the present disclosure will detect volume of urine, duration, and velocity to be analyzed. The systems may also be able to identify disease progress, but also help identify problems in one of the more risky activities of the elderly such as when a user is rushing to the bathroom or placed too firmly or falls onto the seat. As discussed herein, the systems of the present disclosure send out alerts when a user's profile starts to deviate. Through these slight deviations it is possible to send out a warning to the bowel and bladder nurse or other person. The nurse will then go and visit the resident to check on them.

Initially focuses on providing bowel and bladder nurses information that will help them figure out what is wrong with their patient. The dashboard will query and present information to the nurses, so they can make the best diagnosis possible. The device will act as a virtual doctor's assistant by suggesting patterns of disease specific symptoms that fit that ailment. Once the system collects a larger set of data the system will be able to use the large data sets that the system collects, i.e., pictures/video, urination data such as duration, color, and velocity, comfort matrix, weight profile, medication, health problems, demographics, and more to generate an artificial intelligence or AI for the toilet. The AI will be focused on identifying, diagnosing, and correcting health problems quickly and efficiently. The major focus of the AI is to change the elderly care industry from a reactive state of mind to a proactive state of mind.

The diagnosis phase initially focuses on providing bowel and bladder nurses or another health care professional or person with information that will help them figure out what is wrong with their patient. The dashboard 200 will query and present information to the nurses, so they can make the best diagnosis possible. The systems initially act to alert a nurse or other health care professional in a manner similar to a smoke alarm. However, as larger amounts of data are collected specific to an individual resident or user the system will provide suggestive diagnosis. The devices and systems of the present disclosure will act as a virtual doctor's assistant by suggesting patterns of disease specific symptoms that fit an ailment using the collected data such as pictures/video, urination data such as duration, color, and velocity, comfort matrix, weight profile, medication, health problems, demographics, and more to generate an artificial intelligence or AI for the toilet. The AI will typically be able to identify, diagnose, and recommend corrections to health problems quickly and efficiently. The AI changes the elderly care industry from a reactive state to a proactive state.

Figure 17:
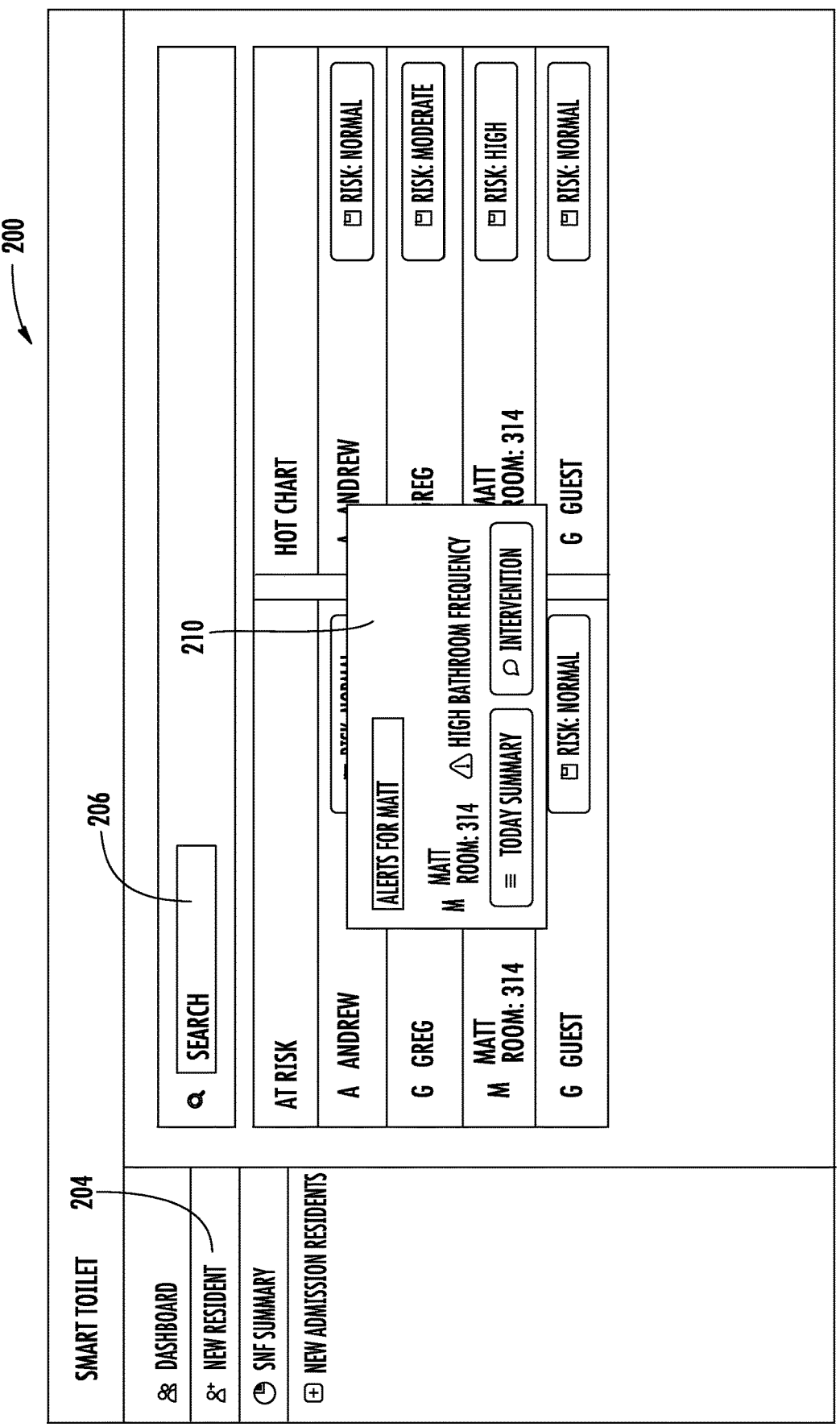
FIG. 17 is an exemplary user dashboard view showing a proactive alert summary to the user, typically a family member or health care professional, for a specific patient or user of a commode device of the present disclosure.

The software systems typically employ a graphical user interface that has a dashboard "home" screen view 200. The dashboard typically has a menu side bar that has a link 204 to a new resident/user data input screen to enter demographic information such as name, birthday, address and location of the user/resident within a care facility. Additionally, the display further includes one or a plurality of individual patient/resident/user data links 202 that, when activated, link to a summary of observed and charted data and analysis for that particular individual (see FIGS. 18-19). The dashboard typically includes a search box data entry field 206. The dashboard also typically provides a realtime data risk assessment indicator for each of the patients/users/residents. The system of the present disclosure will, when necessary, display an individualized alert for an event occurring to a particular resident/patient/user such as the one shown in FIG. 17. The alert summary 210 typically provides direct links to the detailed summary and other information relevant to the observed data of concern to the patient's/resident's health. For example, the summary shows the particular alert, shown in FIG. 17, shows the alert being a high bathroom frequency and provides links to a summary of the day's urination and bowel movement information and room/address information for the user to allow the care professional to readily locate the person.

Figure 18:
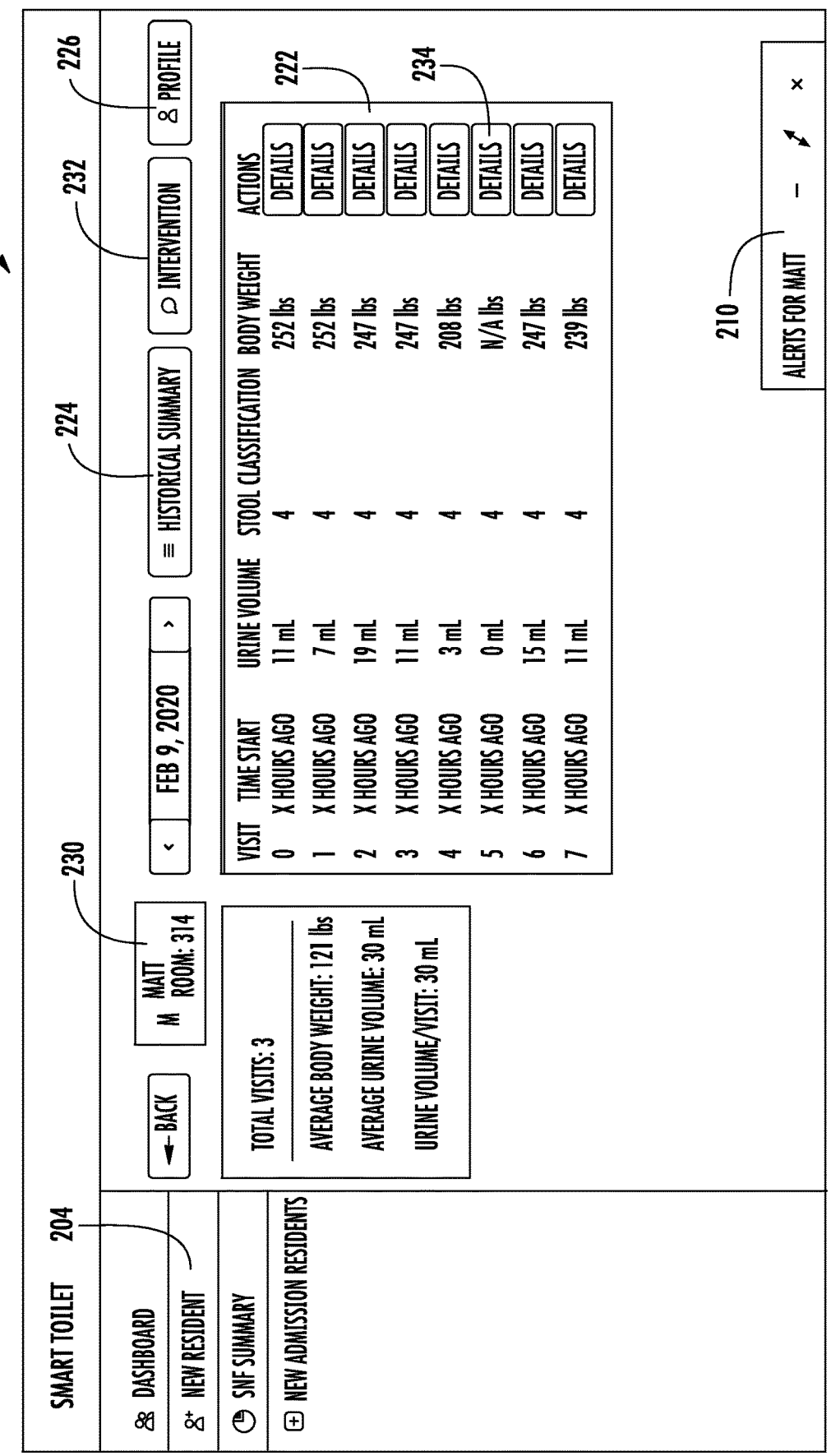
FIG. 18 is an exemplary daily summary for a specific user of the commode device of the present disclosure.

The detailed individual patient profile 220 is shown in FIGS. 18-19. The profile 220 shows a stool and urination evacuation data summary box/chart 222. There is also a link to more historical data 224, a graphical user interface display with personal health and demographic details of the patient 226. There is a date display 228 for the data being shown, which may be for a single date or a range of dates. The screen displays the patient's/resident's name and location 230, which is also typically a link to demographic and family contact information for the resident/patient. There is also typically an intervention link 232. The intervention page is a display page of each recording of what the nurse or nurses do once the systems of the present disclosure identify a problem. If the system identifies a problem, the system of the present disclosure will post a need for an intervention of a certain type to treat a condition on the dashboard. This may or may not be done in the form of an alert. Once the needed intervention is on the dashboard, it is up to the registered nurses to view the alert and act upon it accordingly. This could include giving more water, prunes, laxatives, exercises, fiber, etc. This is part of the diagnosis phase. Once they treat the resident "intervention" each intervention will have a set of rules that will have flags, trigger, alerts associated with them. The system monitors the intervention recommended based upon rules. Follow up to the interventions are provided as well to determine if the actions taken/interventions succeeded. The follow up can include: looking for stools to get larger, volume of urine decreased, the amount of visits to the toilet has increased, length in time, decrease in body weight, increase in body weight, etc. As shown on the bottom of FIG. 18, the alert for an individual as originally shown in FIG. 17 may be minimized.

Figure 20:
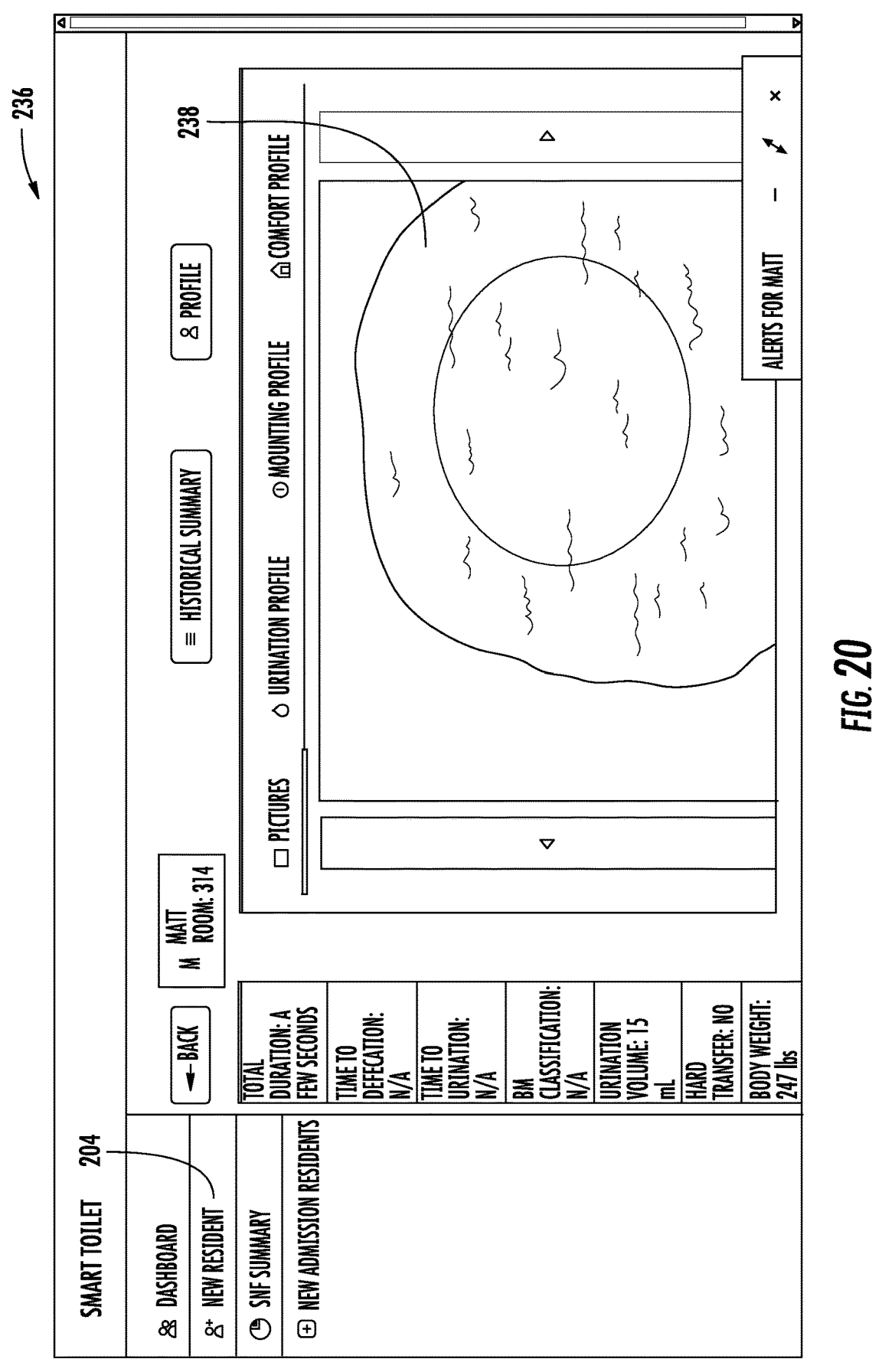
Figure 21:
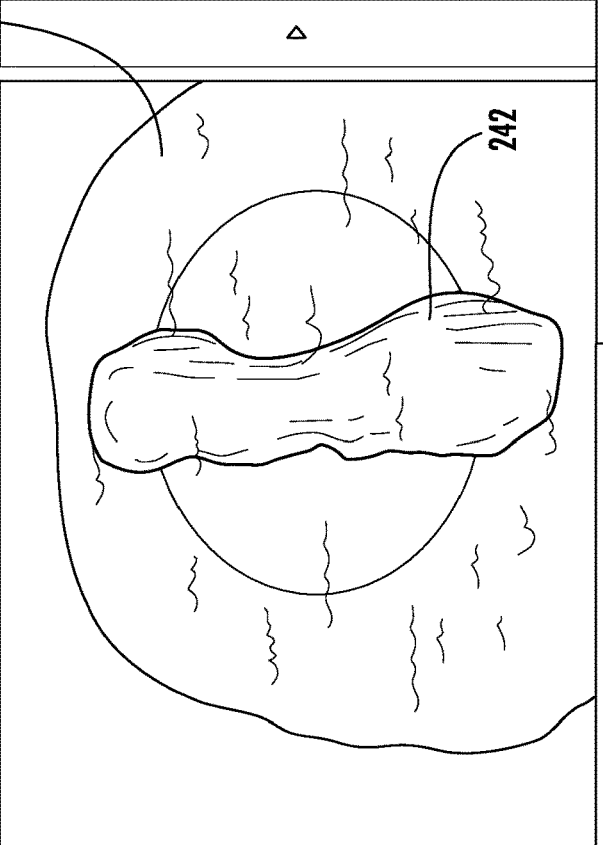
FIG. 21 shows the display detailed view after a stool sample after a bowel movement has occurred when watching a video playback of the bowel movement.

If the details link of an individual stool and/or urine tracking event 234 is activated by the user of the software system, a detailed view 236, such as those shown in FIGS. 20-21, is displayed to the user. At this screen/graphical user interface the user may listen to and/or view images or video recorded data footage of each urination and/or bowel movement. The duration times recorded by the devices are displayed and various other information displayed as well. FIG. 20 shows the video of a bowel movement prior to the bowel movement having occurred 238, while FIG. 21 shows the video of the interior of the toilet bowl after the bowel movement 240 has occurred and shows the stool 242 within the toilet bowl. As discussed above, the video allows health professionals, whether they are remote from the facility where the patient or resident is located to within it to view and analyze each urination and bowel movement to determine if action for the person's health needs to be taken.

It will be understood by one having ordinary skill in the art that construction of the described devices and systems and other components is not limited to any specific material. Other exemplary embodiments of the invention disclosed herein may be formed from a wide variety of materials, unless described otherwise herein. Typically, the systems of the present disclosure are typically produced from plastic components, various sensors, and metal materials, but the particular materials used are often not critical, but generally speaking lighter materials that remain sturdy are most preferred given the portable and retrofittable nature of the devices and systems of the present disclosure.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

It is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method steps or process steps as used herein can be performed in any order, unless otherwise specified or clearly implied to the contrary by the context in which the referenced combination is made.

The devices and systems of the present disclosure described herein, including but not limited to: the commodes; retrofittable commode devices; the related overall systems incorporating the device and used for the monitoring and tracking various health data automatically including bowel movements, bladder evacuations, weight, toilet seat mounting and dismounting data and other health data and alerting health professionals and/or family when potential health changes occurs. The disclosure also may be used as a separate retrofit attachment system for a toilet to transform a standard toilet into a "smart" toilet system. When used to retrofit a commode or toilet seat the system is generally similar to the one shown in FIG. 15. The present disclosure is also generally related to the corresponding manufacturing methods. All of the devices, systems, and methods may comprise, consist of, or consist essentially of the elements of the products as described herein, as well as any additional or optional element described herein or otherwise useful in medical device and health tracking information systems. "Consisting essentially of" in the context of the claims of this application limits the scope of a claim or claim element to the specified materials or steps "and those that do not materially affect the basic and novel characteristic(s)" of the claimed invention as would be known by those of ordinary skill in the art whether or not such a composition is disclosed in the application or not as affecting the basic and novel characteristic.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

The systems of the present disclosure typically include: a retrofittable commode attachment device according to any of the above-discussed embodiments of the present disclosure and also typically a remotely located server system that is connected via a wired or wireless signal connection to a local computer system that may be any handheld mobile computing device such as a mobile phone with a touch screen data input, a tablet device with a touch screen and/or keyboard data input, a laptop computer system or a desktop computer system or conceivably another server system. The remotely located server system may be configured to: analyze any set or subset of one or more type of data such that alerts may be transmitted to any assigned individual or multiple people when a negative health trend or single event is observed.

What is claimed is:

1. A retrofittable commode attachment device for automatically measuring and charting electronically one or more types of health data comprising:
 a base platform that is separate from a toilet seat of a commode and positioned below the toilet seat and wherein the base platform comprises a back portion, a left side portion, a right side portion and a front portion, a plurality of load cells on the left side of the base platform and a plurality of load cells on the right side of the base platform;
 at least one microphone;
 at least one camera; and
 at least two commode connector brackets that engage a horizontal support of the commode;
 wherein the base platform is not part of the toilet seat;
 wherein the plurality of load cells are in signal communication with a signal transmitter engaged with the base platform that delivers data via a wired data signal transfer system or a wireless data signal transfer system to a server system located remote from the retrofittable commode attachment device that stores the one or more types of health data transferred to it from the retrofittable commode attachment device; and
 wherein the at least one microphone and the at least one camera are within a housing mounted to the back portion of the base platform and extending away from the back portion such that the at least one camera and the at least one microphone are positioned to view an inside of a feces or urine receiving commode bucket and does not view a user's buttocks or anus when in use.

2. The retrofittable commode attachment device for automatically measuring and charting electronically one or more types of health data of claim 1, wherein the signal transmitter is powered by a rechargeable battery and the signal transmitter and the rechargeable battery and a microprocessor controller are within an electronic component compartment of the base platform.

3. The retrofittable commode attachment device for automatically measuring and charting electronically one or more types of health data of claim 2, further comprising a housing that includes a curved portion that extends away from the back portion and downwardly from the back portion and a substantially planar portion wherein the curved portion is pliable and allows a user to apply force to the housing to change its position but the housing retains its position unless a force from a user is applied to it.

4. The retrofittable commode attachment device for automatically measuring and charting electronically one or more types of health data of claim 3, wherein the at least one camera and the at least one microphone are flush with a toilet bowl facing surface of the substantially planar portion of the housing and wherein the curved portion is shorter than the planar portion.

5. The retrofittable commode attachment device for automatically measuring and charting electronically one or more types of health data of claim 1, wherein the base platform comprises a left support section, a right support section, a right side moveable section, and a left side moveable section wherein the left side moveable section and the right side moveable section are able to be moved by hand and without the use of tools between an in-use position and a retracted position wherein the retracted position allows for removal of the feces or urine receiving commode bucket from below the base platform without removing the base platform from engagement with the commode and wherein the left side moveable section and the right side moveable section are both generally C-shaped or generally U-shaped.

6. The retrofittable commode attachment device for automatically measuring and charting electronically one or more types of health data of claim 5, wherein the signal transmitter is in communication with a microprocessor within an electrical component compartment and the at least two commode connector brackets are snap fit engagement devices that, when engaged, allow the base platform to rotate about a horizontal support bar of the commode.

7. The retrofittable commode attachment device for automatically measuring and charting electronically one or more types of health data of claim 5, wherein the left side moveable section is engaged with the left support section using at least one left side hinge such that the left side moveable section is moveable from the in-use position which is at least substantially horizontal and the retracted position which is a rotated position that is at least 75 degrees above the in-use position; and wherein the right side moveable section is engaged with the right support section using at least one right side hinge such that the left side moveable section is moveable from the in-use position which is at least substantially horizontal and the retracted position which is a rotated position that is at least 75 degrees above the in-use position.

8. The retrofittable commode attachment device for automatically measuring and charting electronically one or more types of health data of claim 1, wherein the base platform is substantially the same shape as a toilet seat and having a thickness and the toilet seat having a bottom surface that faces a toilet bowl when in use and a downwardly extending lip around a perimeter of the toilet seat and defining a bottom surface cavity of at least approximately the same depth as the thickness of the base platform and configured to receive the base platform therein such that the top of the base platform engages bottom surface when both the retrofittable commode attachment device and the toilet seat are in an in-use position.

9. The retrofittable commode attachment device for automatically measuring and charting electronically one or more types of health data of claim 1, wherein the at least two commode connector brackets are engaged with the horizontal support of the commode such that the base platform, the toilet seat of the commode, and a lid of the commode rotate about the same or substantially the same axis.

10. The retrofittable commode attachment device for automatically measuring and charting electronically one or more types of health data of claim 1, wherein the feces or urine receiving commode bucket comprises at least one load cell in signal communication with the signal transfer wherein the feces or urine receiving commode bucket measures a weight change of the feces or urine receiving commode bucket when a user urinates, defecates or both urinates and defecates into the feces or urine receiving commode bucket.

11. The retrofittable commode attachment device for automatically measuring and charting electronically one or more types of health data of claim 10, wherein the at least one camera, the at least one microphone and a load cell of the feces or urine receiving commode bucket provide data to the remote server that processes audio, visual and weight data to estimate the weight of the urine, stool, or urine and stool added to the feces or urine receiving commode bucket and automatically records the estimated weight of each of the urine and stool and a time of an evacuation of a bladder of a user of the retrofittable commode attachment device, a bowels of the user of the retrofittable commode attachment device or the bladder and the bowels of the user of the retrofittable commode attachment device and allows a health care professional to review the data using a computer system in signal communication with the server system located remote from the retrofittable commode attachment device via a computer network.

12. The retrofittable commode attachment device for automatically measuring and charting electronically one or more types of health data of claim 1, wherein the retrofittable commode attachment device records and transmits to the server system located remote from the retrofittable commode attachment device at least health care data of different types chosen from the group consisting of: weight of a user, weight of urine, timing of urine stream, weight of stool, nature of the stool, shifting of weight of the user on the retrofittable commode attachment device while seated on the retrofittable commode attachment device, mounting forces of each load cell as a user sits on the toilet seat, dismounting forces of each load cell as the user lifts off from the toilet seat and associates a time when each piece of data is collected regarding the timing of use with an individual user of the retrofittable commode attachment device.

13. The retrofittable commode attachment device for automatically measuring and charting electronically one or more types of health data of claim 12, wherein the server system located remote from the retrofittable commode attachment device analyzes the data and establishes a first average of the data for one type of health care data of different types over a first time period and compares the first average of the data for health care data of different types over the first time period to either (1) a single health care data measurement of the same health care data type and/or (2) a second average of the data for the one type of health care data of the data for health care data of different types over a second time period that is shorter than the first time period and, based on differences between the first average of the data and either the single health care data measurement and/or the second average of the server system located remote from the retrofittable commode attachment devices sends an alert to a health care professional's computing device or a person designated by the user of the retrofittable commode attachment device or the user of the retrofittable commode attachment device thereby providing an automated alert when the health of the user is changing.

14. The retrofittable commode attachment device for automatically measuring and charting electronically one or more types of health data of claim 5, wherein the retrofittable commode attachment device records and transmits to the server system located remote from the retrofittable commode attachment device at least health care data of different types chosen from the group consisting of: weight of a user, weight of urine, timing of urine stream, weight of stool, nature of the stool, shifting of weight of the user on the retrofittable commode attachment device while seated on the retrofittable commode attachment device, mounting forces of each load cell as a user sits on the toilet seat, dismounting forces of each load cell as the user lifts off from the toilet seat and associates a time when each piece of data is collected regarding the timing of use with an individual user of the retrofittable commode attachment device.

15. The retrofittable commode attachment device for automatically measuring and charting electronically one or more types of health data of claim 14, wherein the server system located remote from the retrofittable commode attachment device analyzes the data and establishes a first average of the data for one type of health care data of different types over a first time period and compares the first average of the data for health care data of different types over the first time period to either (1) a single health care data measurement of the same health care data type and/or (2) a second average of the data for the one type of the health care data of the data for health care data of different types over a second time period that is shorter than the first time period and, based on differences between the first average of the data and either the single health care data measurement and/or the second average of the server system located remote from the retrofittable commode attachment devices sends an alert to a health care professional's computing device or a person designated by the user of the retrofittable commode attachment device or the user of the retrofittable commode attachment device thereby providing an automated alert when the health of the user is changing.

16. The retrofittable commode attachment device for automatically measuring and charting electronically one or more types of health data of claim 1 further comprising a scale chosen from the group consisting of: (1) a set of foot scales that includes a first foot scale rotatably engaged with a first front leg of the commode and a second foot scale rotatably engaged with a second front leg of the commode; and (2) a planar pad engaged with both the first front leg of the commode and the second front leg of the commode such that the planar pad is moveable between a vertical position where the pad is proximate a length of the first front leg and a length of a second front leg and a horizontal position against a floor or other surface that the first front leg and the second front leg is resting on and wherein the planar pad comprises a plurality of load cells and the first foot scale comprises a load cell and the second foot scale comprises a load cell.

17. The retrofittable commode attachment device for automatically measuring and charting electronically one or more types of health data of claim 5, wherein a load cell of the plurality of load cells is individually within a corresponding seat support wherein each seat support extends upwardly from a top surface of the base platform and the seat supports each have a top surface that engages a bottom surface of a toilet seat and a bottom surface of the base platform is rectangular and has four corner sections and the retrofittable commode attachment device comprises at least four commode connector brackets with each bracket positioned in each of the corner sections of the bottom surface of the base platform and such that two connector brackets engage a rear horizontal support bar of the commode and two connector brackets engage a front horizontal support bar of the commode and the at least four connector brackets comprises a base engaged to the base platform, a first archuous section having a snap fit engagement lip section, a second archuous section having a grasping end wherein the snap fit engagement lip section and the grasping end frictionally engage with one another when the bracket is in a closed position.

18. The retrofittable commode attachment device for automatically measuring and charting electronically one or more types of health data of claim 17 further comprising a scale chosen from the group consisting of: (1) a set of foot scales that includes a first foot scale rotatably engaged with a first front leg of the commode and a second foot scale rotatably engaged with a second front leg of the commode; and (2) a planar pad engaged with both the first front leg of the commode and the second front leg of the commode such that the planar pad is moveable between a vertical position where the pad is proximate a length of the first front leg and a length of a second front leg and a horizontal position against a floor or other surface that the first front leg and the second front leg is resting on and wherein the planar pad comprises a plurality of load cells and the first foot scale comprises a load cell and the second foot scale comprises a load cell.

19. A commode attachment system for automatically measuring and charting electronically one or more types of health data comprising:
   a remote data server having analytics software that analyze data received from a commode attachment data collection device and accessible by a health care professional using a healthcare professional user interface, wherein the healthcare professional user interface displays data related to health data collected by a commode attachment device and conveyed from the commode attachment device to the remote data server; and
   wherein the commode attachment data collection device that is not a portion of a toilet seat or a lid and wherein the commode attachment data collection device comprises:
   a base platform comprising a back portion, a left side portion, a right side portion and a front portion, a plurality of load cells on the left side of the base platform and a plurality of load cells on the right side of the base platform, at least one microphone, at least one camera, and at least two commode connector brackets that engage a horizontal support of a commode wherein the base platform is positioned below the toilet seat of the commode; and wherein the plurality of load cells are in signal communication with a signal transmitter engaged with the base platform that delivers data via a wired data signal transfer system or a wireless data signal transfer system to a server system located remote from the retrofittable commode attachment device that stores the health data transferred to it from the retrofittable commode attachment device; and wherein the at least one microphone and the at least one camera are within a housing mounted to the back portion of the base platform and extending away from the back portion such that the at least one camera and the at least one microphone are positioned to view an inside of a toilet bowel.

20. A commode attachment system for automatically measuring and charting electronically one or more types of health data comprising:
   a remote data server having analytics software that analyze data received from a commode attachment data collection device and accessible by a health care professional using a health care professional user interface, wherein the professional user interface displays data related to health data collected by a commode attachment device and conveyed from the commode attachment device to the remote data server; and
   wherein the commode attachment data collection device is not a portion of a toilet seat or a lid and wherein the commode attachment data collection device comprises:
   a base platform comprising a back portion, a left side portion, a right side portion and a front portion, a plurality of load cells on the left side of the base platform and a plurality of load cells on the right side of the base platform, at least one microphone, at least one camera, and at least two commode connector brackets that engage a horizontal support of a commode wherein the base platform is positioned below the toilet seat of the commode; and wherein the plurality of load cells of the left side of the base platform and the plurality of load cells of the right side of the base platform are in signal communication with a signal transmitter engaged with the base platform that delivers data via a wired data signal transfer system or a wireless data signal transfer system to a server system located remote from the commode attachment device that stores the health data transferred to it from the commode attachment device; and wherein the at least one microphone and the at least one camera are within a housing mounted to the back portion of the base platform and extending away from the back portion such that the at least one camera and the at least one microphone are positioned to view an inside of a toilet bowl; and a scale chosen from the group consisting of: (1) a set of foot scales that includes a first foot scale rotatably engaged with a first front leg of the commode and a second foot scale rotatably engaged with a second front leg of the commode; and (2) a planar pad engaged with both the first front leg of the commode and the second front leg of the commode such that the planar pad is moveable between a vertical position where the pad is proximate a length of the first front leg and a length of a second front leg and a horizontal position against a floor or other surface that the first front leg and the second front leg is resting on and wherein the planar pad comprises a plurality of load cells and the first foot scale comprises a load cell and the second foot scale comprises a load cell; and wherein the commode attachment device records and transmits to the server system located remote from the retrofittable commode attachment device at least health care data of different types chosen from the group consisting of: weight of a user, weight of urine, timing of urine stream, weight of stool, nature of the stool, shifting of weight of the user on the retrofittable commode attachment device while seated on the retrofittable commode attachment device, mounting forces of each load cell as a user sits on the toilet seat, dismounting forces of each load cell as the user lifts off from the toilet seat, and the weight of the user and also associates a time when each piece of data is collected or measured wherein the time is when an individual user of the commode attachment device used the commode and an event causing the data occurred.

* * * * *